US009562911B2

(12) United States Patent
Vojdani

(10) Patent No.: US 9,562,911 B2
(45) Date of Patent: Feb. 7, 2017

(54) SIMULTANEOUS CHARACTERIZATION OF IGG AND IGA ANTIBODIES TO MULTIPLE FOOD ANTIGENS AND C1Q-FOOD PROTEIN IMMUNE COMPLEXES

(71) Applicant: Aristo Vojdani, Los Angeles, CA (US)

(72) Inventor: Aristo Vojdani, Los Angeles, CA (US)

(73) Assignees: Cyrex Laboratories, LLC, Phoenix, AZ (US); Immunosciences Lab, Inc., Los Angeles, CA (US)

( * ) Notice: Subject to any disclaimer, the term of this patent is extended or adjusted under 35 U.S.C. 154(b) by 0 days.

(21) Appl. No.: 14/609,865

(22) Filed: Jan. 30, 2015

(65) Prior Publication Data

US 2016/0320403 A1    Nov. 3, 2016

(51) Int. Cl.
G01N 33/68 (2006.01)
G01N 33/544 (2006.01)

(52) U.S. Cl.
CPC ........ *G01N 33/6854* (2013.01); *G01N 33/544* (2013.01)

(58) Field of Classification Search
None
See application file for complete search history.

(56) References Cited

U.S. PATENT DOCUMENTS 8,309,318 B2    11/2012   Dorval et al.
2005/0119475 A1   6/2005   Ishikawa et al.

OTHER PUBLICATIONS

Aristo Vojdani, "Detection of IgE, IgG, IgA and IgM antibodies against raw and processed food antigens, Nutrition & Metabolism", Biomed Central, London, GB, vol. 6, No. 1, May 12, 2009, pp. 22.
Kodama et al., "Role of complement in a murine model of peanut-induced anaphylaxis", Immunobiology, Urban Und Fischer Verlag, vol. 218, No. 6, Oct. 17, 2012, pp. 844-850.
L Meulenbroek et al., "Complement and complement receptors CD21 and CD35 are involved in IgE-facilitated allergen binding to B cells in food allergy", Allergy, vol. 66, No. S94, Jun. 15, 2011, pp. 228.
Severance et al., "Complement C1q formation of immune complexes with milk caseins and wheat glutens in schizophrenia", Neurobiology of Disease, vol . 48, No. 3, Dec. 1, 2012, pp. 447-453.
European Patent Office, International Search Report and Written Opinion for International Application No. PCT/US2015/013770, Sep. 29, 2015, 10 pages.
Vojdani, Lectins, agglutinins, and their role in autoimmune reactivities. Alternative Therapies in Health and Medicine, (In Press), 2015.
Novik et al., A novel procedure for the isolation of glycolipids from Bifidobacterium adolescentis 94 BIM using supercritical carbon dioxide. J Biotechnol. 2006;121(4):555-62.
Vojdani, A potential link between environmental triggers and autoimmunity.Autoimmune Diseases. vol. 2014, Article ID 437231, 18 pages. http://dx.doi.org/10.115/2014/437231, 2014.
Fabian C et al., A review on rice bran protein: its properties and extraction methods. Crit Rev Food Sci Nutr. 2011;51:816-827.
Vojdani et al., Antibodies to neuron-specific antigens in children with autism: Possible cross reaction with encephalitogenic proteins from milk. Chlamydia pneumonia and *Streptococcus* Group A. J. Neuroimmunol. 2002;129:168-177.
Baboonian C et al., Antibodies in rheumatoid arthritis react specifically with the glycine alanine repeat sequence of Epstein-Bar nuclear antigen-1. Rheumatol Int. 1989;9:161.
Bradl M, Lassmann DH. Anti-aquaporin-4 antibodies in neuromyelitis optica: how to prove their pathogenetic relevance? Int. MS J. 2008;15:75-78.
Kinoshita M et al., Anti-aquaporin-4 antibody induces astrocytic cytotoxicity in the absence of CNS antigen-specific T cells. Biochem. Biophys. Re.s Commun. 2010;394:205-210.
Jarius S, Wildermann B., AQP4 antibodies in neuromyelitis optica: diagnostic and pathogenetic relevance. Nat. Rev. Neurol. 2010;6:383-392.
Viashnav et al., Aquaporin-4 molecular mimicry and implication for neuromyelitis optics. J. Neuroimmunol. 2013;26:92-98.
Sugai et al., Bone-specific antibodies in sera from patients with celiac disease: characterization and implications in osteoporosis. J Clin Immunol. 2002;22:353-362.
Bousquet et al., Scientific criteria and selection of allergenic foods for product labelling. Allergy. 1998;53,3-21.
Maul et al., Can loss of immune tolerance cause IBD? Inflamm Bowel Dis. 2008;14(2):S115-S116.
Frustaci et al., Celiac disease associated with autoimmune myocarditis circulation. 2002;2:2611-2618.
De Freitas et al., Celiac disease in Brazilian adults. J Clin Gasroenterol. 2002;34:430-434.
Arentz-Hansen et al., Celiac lesion T cells recognize epitopes that cluster in regions of gliadins rich in proline residues. Gastroenterology. 2002;123(3)803-809.
Hamada, Characterization of protein fractions of rice bran to devise effective methods of protein solubilization. Cereal Chem. 1997;74:662-668.
Vojdani, The characterization of repertoire of what antigen and peptide involved in the humoral immune response in patients with gluten sensitivity and Crohn's disease. ISRN Allergy. 2011;2011,950104.
Kim et al., Clinical spectrum of CNS aquaporin-4 autoimmunity. Neurol. 2012;78:1179-1185.
Ho et al., Clinical spectrum of food allergies: a comprehensive review. Clin. Rev. Allergy Immunol. 2012;DOI:10.1007/s12016-012-8339-6.
Jack et al., Cloning and analysis of cDNA encoding bovine butyrophilin, and apical glycoprotein expressed in mammary tissue and secreted in association with the milk-fat globule membrane during lactation. J. Biol. Chem. 1990;265:14481.

(Continued)

*Primary Examiner* — Jacob Cheu
(74) *Attorney, Agent, or Firm* — Fish & Tsang, LLP

(57) ABSTRACT

Compositions and methods for accurately characterizing immune reactivity to food allergens have been developed, in which test surfaces that incorporate different food antigen preparations derived from the same food into individual test sites are provided. Such coated surfaces can be produced using raw and cooked foods. The use of a panel of such test surfaces to characterize specific IgG, IgA, and/or C1q binding provides improved sensitivity and accuracy in determining immune reactivity and response to specific foods.

12 Claims, 11 Drawing Sheets

(56) References Cited

OTHER PUBLICATIONS

Collin et al., Endocrinological disorders and celiac disease. Endoc Rev. 2002;23:464-483.
Dubois et al., Colorimetric method for determination of sugar and related substances. Anal Chem. 28(3): 350-356, 1956.
Smit et al., Contribution of classic and alternative effector pathways in peanut-induced anaphylactic responses. PLoS ONE. 2011;6:e28917.
Malosse et al., Correlation between milk and dairy product consumption and multiple sclerosis prevalence: a worldwide study. Neuroepidemiol. 1992;11:304-312.
Ruddell et al., Coeliac disease and autoimmune thyroid disease. Gut. 1994;35:844-846.
Baboonian et al., Cross reaction of antibodies to glycine/alanine repeat sequence of Epstein-Barr virus nuclear antigen-1 with collagen, cytokeratin, and actin. Ann Rheum Dis. 1991;50:772.
Vojdani et al., Cross-reaction between gliadin and different food and tissue antigens. Food Nutr Sci. 2013;44,20-32.
Fleurat-Lassard et al., The distribution of aquaporin subtypes (PIP1, PIP2 and gamma-TIP) is tissue dependent in soybean (*Glycine max*) root nodules. Ann. Bot. 2005;96:457-460. 64. Fabian.
Butcher J., The distribution of multiple sclerosis in relation to the dairy industry and milk consumption. N.Z. Med. J. 1976;83:427-430.
Schrander et al., Does food intolerance play a role in juvenile chronic arthritis? Br J Rheumatol. 1997;36:905.
Lim et al., The effect of antibody on the intestinal absorption of macromolecules and on intestinal permeability in adult mice. Int Arch Allergy Appl Immunol 1982;68.41-46.
Lunardi et al., Elimination diet in the treatment of selected patients with hypersensitivity vasculitis. Clin Exp Rheumatol. 1992;10:131.
Lack G., Epidemiologic risks for food allergy. J Allergy Clin Immunol. 2008;121:1331-1336.
Ostenstad et al., Evidence for monoclonal expansion of synovial T cells bearing V alpha 2.1N beta 5.5 gene segments and recognizing a synthetic peptide that shares homology with a number of putative autoantigens. Immunology. 1995;86:168.
Vojdani, Food immune reactivity and neuroautoimmunity. Funct Neurol Rehabil Ergon. 2014;4(2-3):175-195.
E.G. Knox, Foods and diseases. Br. J. Prev. Soc. Med. 1977;31:71-80.
Hadjivassiliou et al., Gluten sensitivity masquerading as systemic lupus erythematosus . Ann Rhem Dis. 2004;63:1501-1503.
Jacob et al., Gluten sensitivity and neuromyelitis optica: two case reports. J Neurol Neurosurg Psychiatry. 2005;76:1028-1030.
Hadjivassiliou et al., Gluten ataxia. Cerebellum. 2008;7:494-98.
Stamnaes et al., Gluten T cell epitope targeting by TG3 and TG6; implications for dermatitis herpetiformis and gluten ataxia. Proceedings of the 13th International Symposium on Coeliac Disease. Amsterdam. 2009;P-163:148.
Lunardi et al., Glycine-rich cell wall proteins act as specific antigen targets in autoimmune and food allergic disorders. Int Immunol. 2000;12:647-657.
Gillett et al., High prevalence of celiac disease in patients with type I diabetes detected by antibodies to endomysium and tissue transglutaminase. Can J Gastorenterol. 2001;15:297-301.
Mancardi et al., The high-affinity human IgG receptor FcgRI (CD64) promotes IgGmediated inflammation, anaphylaxis, and antitumor immunotherapy. Blood. 2013;121:1563-1573.
Tollefsen et al., HLA-DQ2 and -DQ8 signatures of gluten T cell epitopes in celiac disease. J Clin Invest. 2006;116(8)2226-2236.
Amor et al., Identification of epitopes of myelin oligodendrocyte glycoprotein for the induction of experimental allergic encephalomyelitis in SJL and Biozzi AB/H mice. J. Immunol. 1994;153:4349.
Natter et al., IgA cross-reactivity between a nuclear autoantigen and wheat protein suggests molecular mimicry as a possible pathomechanism in celiac disease. Eur J Immunol. 2001;31:918-928.
R.M.R. Barnes, IgG and IgA antibodies to dietary antigens in food allergy and intolerance. Clin Exp Allergy. 1995;25:7-9.
Vojdani et al., Immune response to dietary proteins, gliadin and cerebellar peptides in children with autism. Nutr. Neurosci. 2004;7,151-161.
Reinke et al., Impairment of protein trafficking by direct interaction of gliadin peptide with actin. Exp Cell Res. 2011;DOI:10.1016/J.YXCT.2011.05.022.
Arentz-Hansen et al., The intestinal T cell response to α-gliadin in adult celiac disease is focused on a single deamidated glutamine targeted by tissue transglutaminase. J Exp Med. 2000;191(4)603-312.
Camarca et al., Intestinal T cell responses to gluten peptides are largely heterogeneous: implications for a peptide-based therapy in celiac disease. J Immunol. 2009;182(7)4158-4166.
Novik et al., Isolation and comparative analysis of glycolipids from bifidobacteria. Mikrobiology. 2005;74(5):1-8.
Muthukumar et al., Isolation, purification and biochemical characterization of lectin from oyster mushroom, Pleurotus sajor-caju. Plant Archives 2009;9:41-46.
Jarius et al., Mechanisms of disease: aquaporin-4 antibodies in neuromyelitis optica. Nat. Clin. Pract. Neurol. 2008;4:202-214.
Gardinier et al., Myelin/oligodendrocyte glycoprotein is a unique member of the immunoglobulin super-family. J. Neurosci. Res. 1992;33:177.
Kahana et al., Multiple sclerosis: genetic versus environmental aetiology. Epidemiology in Israel updated. J Neurol. 1994;241:341-346.
Brandtzaeg et al., Mucosal penetrability enhanced by serum-derived antibodies. Nature. 1977;266.262-263.
Tsuji et al., Oral tolerance: intestinal homeostasis and antigen-specific regulatory T cells. Trends Immunol. 2008;29(11):532-540. Doi10.1016/j.it2008.09.002.
Strait et al., Pathways of anaphylaxis in the mouse. J. Allergy Clin. Immunol. 2002;109: 658-668.
Chaiklahan et al., Polysaccharide extraction from *Spirulina* sp. and its antioxidant capacity. Int J Biol Macromol. 58: 73-78, 2013.
Derek Lamport, Preparation of arabinogalactan glycoproteins from plant tissues. Bio-Protocol. 3(19):Oct. 5, 2013, e918.
Zuidmeer et al., The prevalence of plant food allergies: A systemic review. J Allergy Clin Immunol. 2008;121,1210-1218.
Vojdani et al., The prevalence of antibodies against wheat and milk proteins in blood donors and their contribution to neuroautoimmune reactivities. Nutrients. 2014;6:15-36.
Tang et al., Protein extraction from heat-stabilized defatted rice bran. I. Physical processing and enzyme treatments. J Agric Food Chem. 2002;50:7444-7448.
Pratesi et al., Serum IgA antibodies from patients with coeliac disease react strongly with human brain blood-vessel structures. 1998;33:817-821.
Henry et al., Structure and evolution of the extended B7 family. Immunol. Today. 1999;20:285.
Plasencia et al., Structure and stability of the spinach aquaporin SoPIP2:1 in detergent micelles and lipid membranes. PLoS One. 2011;6:e14674.
Miyajima et al., Systemic anaphylaxis in the mouse can be mediated largely through IgG1 and Fc gammaRIII. Assessment of the cardiopulmonary changes, mast cell degranulation, and death associated with active or IgE- or IgG1-dependent passive anaphylaxis. J. Clin. Invest. 1997;99:901-914.
Johnston et al., The immunology of food allergy. J. Immunol. 2014;192:2529-2534.
Stagi et al., Thyroid function, autoimmune thyroiditis and coeliac disease in juvenile idiopathic arthritis. Rheumatology. 2005;44:517-520.
Singh et al., Use of sonication and size-exclusion HPLC in the study of wheat flour protein. I. Dissolution of total protein in unreduced form. Cereal Chem. 1990;67:150-161.
Aleadini et al., Immune cross-reactivity in celiac disease: anti-gliadin antibodies bind to neuronal synapsin I. May 15, 2007;178(10):6590-5.

(56) References Cited

OTHER PUBLICATIONS

Agranoff et al., Diet and the geographical distribution of multiple sclerosis. The Lancet. vol. 304, Issue 7888, Nov. 2, 1974, pp. 1061-1066.

Sheng et al., Preparation, identification and their antitumor activities in vitro of polysaccharides from Chlorella pyrenoidosa. Food Chem. 105(2): 533-539, 2007.

| Antigen Set 1: Level of IgG/IgA antibodies against various food extracts expressed as optical density | | | | | | | | |
|---|---|---|---|---|---|---|---|---|
| Food | 1 Commercial Food Antigen Preparations | 2 Water Soluble Food Antigens | 3 Alcohol Soluble Food Antigens | 4 Alkali Soluble Food Antigens | 5 Food Glyco-lipids | 6 Food Poly-saccharides | 7 Food Glyco-proteins | Mixture of 2 to 7 | Mixture of 2 to 7 Heat-Denatured |
| Apple | 0.21 | 0.18 | 0.32 | 0.16. | 0.27 | 0.34 | 0.17 | 0.45 | 0.29 |
| Apricot | 0.43 | 0.51 | 0.27 | 0.22 | 0.18 | 0.15 | 0.11 | 0.68 | 0.52 |
| Banana | 0.58 | 0.63 | 0.36 | 0.20 | 0.14 | 0.98 | 0.24 | 1.73 | 1.48 |
| Bean, Lima | 0.33 | 0.21 | 0.18 | 0.19 | 0.27 | 0.24 | 0.35 | 0.39 | 0.44 |
| Blueberry | 0.17 | 0.24 | 0.15 | 0.25 | 0.16 | 0.27 | 0.30 | 0.46 | 0.42 |
| Broccoli | 0.59 | 0.28 | 0.26 | 0.33 | 0.21 | 0.35 | 0.22 | 0.67 | 0.63 |
| Cabbage | 0.14 | 0.16 | 0.13 | 0.18 | 0.11 | 0.24 | 0.13 | 0.26 | 0.29 |
| Cantaloupe | 0.16 | 0.55 | 0.23 | 0.31 | 0.17 | 0.15 | 0.23 | 0.71 | 0.74 |
| Carrot | 0.22 | 0.14 | 0.15 | 0.23 | 0.10 | 0.14 | 0.12 | 0.35 | 0.31 |
| Cauliflower, CK | 0.25 | 0.29 | 0.21 | 0.12 | 0.13 | 0.16 | 0.11 | 0.27 | 0.26 |
| Celery | 0.40 | 0.43 | 0.27 | 0.32 | 0.18 | 0.19 | 0.22 | 0.52 | 0.47 |
| Cherry | 0.13 | 0.15 | 0.21 | 0.15 | 0.12 | 0.23 | 0.21 | 0.31 | 0.28 |
| Chocolate/ Cocoa | 0.37 | 0.32 | 0.17 | 0.21 | 0.15 | 0.11 | 0.18 | 0.33 | 0.30 |
| Coffee | 0.95 | 1.24 | 0.84 | 0.75 | 0.53 | 0.28 | 0.79 | 3.23 | 2.81 |
| Corn | 0.48 | 0.56 | 1.40 | 0.93 | 0.72 | 0.86 | 0.24 | 2.84 | 2.27 |
| Cranberry | 0.35 | 0.31 | 0.22 | 0.17 | 0.15 | 0.26 | 0.20 | 0.35 | 0.30 |
| Cucumber | 0.10 | 0.15 | 0.13 | 0.22 | 0.14 | 0.22 | 0.15 | 0.31 | 0.28 |
| Garlic | 0.29 | 0.25 | 0.19 | 0.23 | 0.20 | 0.17 | 0.10 | 0.28 | 0.17 |

FIG. 8

| Antigen Set 2: Level of IgG/IgA antibodies against various food extracts expressed as optical density | | | | | | | | |
|---|---|---|---|---|---|---|---|---|
| Food | 1 Commercial Food Antigen Preparations | 2 Water Soluble Food Antigens | 3 Alcohol Soluble Food Antigens | 4 Alkali Soluble Food Antigens | 5 Food Glyco-lipids | 6 Food Poly-saccharides | 7 Food Glyco-proteins | Mixture of 2 to 7 | Mixture of 2 to 7 Heat-Denatured |
| Ginger | 0.14 | 0.09 | 0.05 | 0.16 | 0.15 | 0.17 | 0.08 | 0.34 | 0.30 |
| Grape | 0.08 | 0.16 | 0.11 | 0.23 | 0.19 | 0.23 | 0.17 | 0.25 | 0.28 |
| Grapefruit | 0.37 | 0.28 | 0.22 | 0.18 | 0.07 | 0.03 | 0.26 | 0.21 | 0.25 |
| Lemon | 0.02 | 0.07 | 0.13 | 0.16 | 0.01 | 0.15 | 0.24 | 0.20 | 0.18 |
| Lettuce | 0.30 | 0.26 | 0.21 | 0.19 | 0.13 | 0.18 | 0.26 | 0.12 | 0.10 |
| Mushroom | 0.45 | 0.38 | 1.25 | 0.27 | 0.32 | 2.48 | 0.98 | 3.11 | 3.52 |
| Mustard | 0.88 | 0.94 | 0.16 | 0.07 | 0.19 | 0.24 | 0.39 | 1.15 | 1.0 |
| Nutmeg | 0.35 | 0.21 | 0.99 | 0.13 | 0.01 | 0.06 | 1.28 | 1.97 | 2.61 |
| Olive | 0.27 | 0.25 | 0.31 | 0.39 | 0.16 | 0.14 | 0.11 | 0.42 | 0.39 |
| Onion | 0.15 | 0.23 | 0.16 | 0.09 | 0.07 | 0.11 | 0.14 | 0.36 | 0.32 |
| Orange | 0.08 | 0.11 | 0.03 | 0.06 | 0.10 | 0.13 | 0.15 | 0.07 | 0.16 |
| Pea | 0.86 | 0.73 | 1.98 | 0.62 | 0.39 | 0.87 | 1.85 | 2.67 | 2.89 |
| Peach | 0.05 | 0.10 | 0.14 | 0.12 | 0.26 | 0.21 | 0.20 | 0.36 | 0.29 |
| Pear | 0.17 | 0.26 | 0.18 | 0.23 | 0.01 | 0.03 | 0.09 | 0.45 | 0.40 |
| Bell Pepper | 0.36 | 0.28 | 0.31 | 0.29 | 0.33 | 0.08 | 0.17 | 0.23 | 0.34 |
| Pineapple | 0.22 | 0.17 | 0.20 | 0.14 | 0.36 | 0.23 | 0.18 | 0.30 | 0.28 |
| Potato, Sweet | 0.12 | 0.10 | 0.19 | 0.23 | 0.20 | 0.15 | 0.16 | 0.25 | 0.17 |
| Potato, White | 0.30 | 0.27 | 0.24 | 0.22 | 0.19 | 0.96 | 0.33 | 1.27 | 1.48 |

FIG. 9

| Antigen Set 3: Level of IgG/IgA antibodies against various food extracts expressed as optical density ||||||||||
|---|---|---|---|---|---|---|---|---|---|
| Food | 1 Commercial Food Antigen Preparations | 2 Water Soluble Food Antigens | 3 Alcohol Soluble Food Antigens | 4 Alkali Soluble Food Antigens | 5 Food Glyco-lipids | 6 Food Poly-saccharides | 7 Food Glyco-proteins | Mixture of 2 to 7 | Mixture of 2 to 7 Heat-Denatured |
| Rice | 1.12 | 1.24 | 1.7 | 0.41 | 0.22 | 0.26 | 0.87 | 3.45 | 2.68 |
| Sesame Seed | 0.25 | 0.29 | 0.33 | 0.26 | 1.63 | 0.13 | 0.35 | 1.91 | 2.14 |
| Soybean | 0.18 | 0.15 | 0.08 | 0.16 | 0.05 | 0.23 | 0.16 | 0.17 | 0.26 |
| Spinach | 0.27 | 0.33 | 0.14 | 0.11 | 1.61 | 0.19 | 0.20 | 1.82 | 1.35 |
| Squash | 0.15 | 0.18 | 0.11 | 0.14 | 0.23 | 0.21 | 0.18 | 0.15 | 0.32 |
| Strawberry | 0.36 | 0.30 | 0.26 | 0.21 | 0.28 | 0.14 | 0.16 | 0.24 | 0.20 |
| Tomato | 0.23 | 0.16 | 0.11 | 0.18 | 0.96 | 0.15 | 0.35 | 1.21 | 1.17 |
| Vanilla | 0.31 | 0.24 | 0.20 | 0.17 | 0.12 | 0.19 | 0.12 | 0.36 | 0.31 |
| Watermelon | 0.17 | 0.12 | 0.15 | 0.18 | 0.11 | 0.17 | 0.19 | 0.23 | 0.27 |
| Wheat | 0.41 | 0.36 | 1.80 | 0.95 | 0.73 | 0.28 | 0.68 | 2.82 | 2.15 |
| Beef | 0.58 | 0.62 | 0.28 | 0.25 | 0.36 | 0.11 | 0.53 | 0.68 | 0.31 |
| Lamb | 0.47 | 0.51 | 0.20 | 0.26 | 0.48 | 0.09 | 0.45 | 0.57 | 0.28 |
| Pork | 0.54 | 0.39 | 0.17 | 0.23 | 0.31 | 0.05 | 0.36 | 0.48 | 0.32 |
| Chicken Meat | 0.19 | 0.18 | 0.12 | 0.15 | 0.08 | 0.16 | 0.06 | 0.15 | 0.23 |
| Egg White | 1.95 | 2.13 | 0.28 | 0.31 | 0.14 | 0.04 | 0.08 | 2.19 | 1.37 |
| Egg Yolk | 0.36 | 0.28 | 2.75 | 0.26 | 0.98 | 0.09 | 0.25 | 3.31 | 1.49 |
| Turkey Meat | 0.23 | 0.15 | 0.20 | 0.33 | 0.24 | 0.06 | 0.18 | 0.35 | 0.22 |
| Bass | 0.31 | 0.28 | 0.36 | 0.25 | 0.17 | 0.11 | 0.13 | 0.42 | 0.37 |

FIG. 10

| Antigen Set 4: Level of IgG/IgA antibodies against various food extracts expressed as optical density | | | | | | | | |
|---|---|---|---|---|---|---|---|---|
| Food | 1 Commercial Food Antigen Preparations | 2 Water Soluble Food Antigens | 3 Alcohol Soluble Food Antigens | 4 Alkali Soluble Food Antigens | 5 Food Glyco-lipids | 6 Food Poly-saccharides | 7 Food Glyco-proteins | Mixture of 2 to 7 | Mixture of 2 to 7 Heat-Denatured |
| Clam | 0.21 | 0.14 | 0.11 | 0.18 | 0.27 | 0.25 | 0.19 | 0.32 | 0.30 |
| Cod | 0.16 | 0.09 | 0.06 | 0.02 | 0.01 | 0.14 | 0.12 | 0.18 | 0.15 |
| Crab | 0.35 | 0.31 | 0.18 | 0.12 | 0.19 | 0.22 | 0.08 | 0.27 | 0.24 |
| Lobster | 0.12 | 0.17 | 0.22 | 0.18 | 0.15 | 0.20 | 0.14 | 0.17 | 0.15 |
| Mackerel | 0.19 | 0.07 | 0.04 | 0.06 | 0.15 | 0.12 | 0.13 | 0.14 | 0.27 |
| Oyster | 0.06 | 0.13 | 0.09 | 0.10 | 0.13 | 0.18 | 0.23 | 0.25 | 0.19 |
| Salmon | 0.10 | 0.16 | 0.12 | 0.23 | 0.20 | 0.19 | 0.17 | 0.28 | 0.35 |
| Scallop | 0.27 | 0.24 | 0.22 | 0.25 | 0.08 | 0.11 | 0.16 | 0.23 | 0.20 |
| Shrimp | 0.25 | 0.30 | 0.86 | 0.20 | 1.72 | 0.07 | 0.49 | 2.76 | 1.21 |
| Trout | 0.19 | 0.15 | 0.08 | 0.05 | 0.03 | 0.00 | 0.26 | 0.13 | 0.29 |
| Tuna | 0.16 | 0.06 | 0.04 | 0.03 | 0.07 | 0.02 | 0.15 | 0.11 | 0.12 |
| Almond | 0.20 | 0.26 | 0.12 | 0.07 | 0.49 | 0.32 | 0.36 | 0.58 | 1.60 |
| Brazil Nut | 0.55 | 0.63 | 0.07 | 0.13 | 0.73 | 0.34 | 0.81 | 1.36 | 2.49 |
| Cashew | 0.23 | 0.16 | 0.19 | 0.21 | 0.34 | 0.26 | 0.33 | 0.18 | 0.21 |
| Coconut | 0.05 | 0.06 | 0.03 | 0.01 | 0.00 | 0.12 | 0.10 | 0.14 | 0.11 |
| Hazelnut | 0.18 | 0.12 | 0.15 | 0.22 | 0.18 | 0.24 | 0.26 | 0.23 | 0.25 |
| Peanut | 1.51 | 2.06 | 0.76 | 0.58 | 0.94 | 0.48 | 1.99 | 2.18 | 3.98 |
| Pecan | 0.46 | 0.49 | 0.15 | 0.14 | 0.12 | 0.11 | 0.27 | 0.64 | 0.83 |

FIG. 11

SIMULTANEOUS CHARACTERIZATION OF IGG AND IGA ANTIBODIES TO MULTIPLE FOOD ANTIGENS AND C1Q-FOOD PROTEIN IMMUNE COMPLEXES

FIELD OF THE INVENTION

The field of the invention is assays for food allergies, particularly delayed hypersensitivity reactions to food antigens.

BACKGROUND

The following description includes information that may be useful in understanding the present invention. It is not an admission that any of the information provided herein is prior art or relevant to the presently claimed invention, or that any publication specifically or implicitly referenced is prior art.

Autoimmune disorders, including neuroautoimmune diseases, affect 7-10% of the world population. Increasingly, such disorders are becoming associated with immune reactivity to commonly consumed foods. Ordinarily the gut mucosal immune system maintains immune homeostasis by inducing tolerance to antigens found in dietary proteins and peptides and commensal flora, while at the same time exerting immune defense against pathogens. The body's normal tolerance of "friendly" antigenic substances can, however, be disrupted by a number of factors. Intestinal barrier dysfunction and breakdown of gut-associated barriers can allow the entry of undigested proteins and peptides into circulation. Under these circumstances the ingestion of these food substances can result in the production of IgG and IgA antibodies, not only against the various food antigens but also against the body's own tissues (a phenomenon known as food autoimmune reactivity). This is due to homology (which is present to varying extents) between the amino acid sequences of many commonly consumed foods and those of many proteins that occur naturally in human tissue, including neural cells. As a result of this antigenic similarity or molecular mimicry between these various food proteins and different target tissue antigens, failing to detect food immune reactivities can initially result in the development of autoimmune reactivities and potentially lead to autoimmune (for example neuroautoimmune) diseases (Vojdani, 2014a; Vojdani, 2014b). As a result, food immune reactivities are receiving an increasing amount of attention, due to both their increasing prevalence and their adverse effect on health and quality of life (Johnson et al., 2014; Vojdani et al., 2014c).

All publications identified herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

The mechanism of immune reactivity is generally biphasic: an acute reaction occurs immediately following allergen exposure, followed by late phase reaction several hours later. During the acute reaction symptoms occur due to the binding of IgE and/or IgG to various cells and the release of mediators, such as histamine and platelet-activating factor (PAF), by mast cells, neutrophils and basophils The late phase involves the influx of inflammatory cytokines such as IL-4, IL-9, IL-33, and TNF-α, and cells such as neutrophils and eosinophils (Ho et al., 2012). In classical delayed food immune reactivity, production of high levels of IgG, IgM or IgA against various food antigens results in C1q binding to the antibody, with the formation of immune complexes and the deposition of immune complexes in various tissue sites. Symptoms can continue for days or even weeks following the initial immune reaction to such food antigens.

IgE, IgG, IgA or IgM play various roles in food immune reactivity (Mijayima et al., 1997). IgE functions via its high-affinity receptor, FcεRI, which is highly expressed on mast cells and basophils. IgG has several receptors, including the high-affinity FcγRI and FcγRIV receptors and the low-affinity FcγRIIB and FcγRIII receptors. All of these receptors are expressed on several types of cells involved in anaphylaxis, including mast cells, basophils, neutrophils, and macrophages.

Five different pathways are involved in food immune reactivity (Mancardi et al., 2013; Smit et al, 2011; Strait et al., 2002):
1. Classical pathway—involving IgE and its receptor FcεRI, mast cells and histamine
2. Alternative pathway—mediated by IgG1, FcγRIII, macrophages and the PAF pathway
3. IgG-basophil-PAF pathway
4. IgG-neutrophil-PAF pathway via FcγRIV
5. IgG, IgM or IgA-immune complex neutrophil pathway.

All these reactions against dietary components can result from a failure of oral tolerance.

As noted above, the gut mucosal immune system normally maintains an immune homeostasis, which consists of maintaining tolerance to harmless or even beneficial molecules in the gut while mounting effective and appropriate immune responses against harmful pathogens (Lim and Rowley, 1982). A lack of response to food antigens with subsequent down-regulation of systemic immune response is what is characterized as oral tolerance. A failure in oral tolerance can result in immune reactivity to ingested food, with potentially life-threatening consequences such as allergies and autoimmunities (Tsuji and Kosaka, 2008).

When these different mechanisms of action fail to control ingested antigens, the result can initially be a breakdown in tolerance to soluble antigens, which activates secretory and systemic immune responses against food antigens. Individuals in whom the immune exclusion mechanism does not function can experience chronic hyperabsorption of macromolecules and the tendency to develop autoantibodies and even autoimmune disease (Maul and Dichmann, 2008). For this reason, the induction of IgG, IgM and IgA antibodies and immune complex formation to the actual food antigen and even cross-priming against bystander antigens may be of clinical significance. Both in vitro and in vivo experimental studies have demonstrated that IgG antibodies that are not balanced by a mucosal IgA response can enhance the epithelial penetration of bystander proteins (Brandtzaeg and Tolo, 1997). The passage of bacterial toxins and various food antigens through the epithelial cells can result in many immune disorders, including autoimmunities.

The type of systemic immune reaction against dietary proteins and peptides depends on the antigenic structure (e.g., protein antigens, particulate antigens, polysaccharides, glycoproteins, glycolipids or enzymes) and the genetic makeup of the individuals. For example, one person may produce IgG while another may produce IgA or IgM antibodies against dietary components (Barnes, 1995). If such IgG, IgM and IgA antibodies against dietary antigens are left undetected, the results can be the development of autoimmunity followed by autoimmune disease.

As a result, in recent decades significant progress has been made in the identification of target peptides in food antigens that share a similarity with autoantigens that are involved in autoimmune diseases (Baboonian et al., 1989; Baboonian et al., 1991; Lunardi et al., 1992; Lunardi et al., 2000; Ostenstad et al., 1995; Schrander et al., 1997). The glycine-rich cell wall protein peptide (GRP) represents an example of an antigenic peptide sequence that is able to prime T- and B-cell immune response in completely different and unrelated diseases. GRP is a ubiquitous food protein found in beans, fruits, vegetables and in gelatin. It has a very high degree of antigenic similarity/homology to ribonucleoprotein, fibrillar collagen, cytokeratin and EBV nuclear antigen-1 (EBNA-1) which are common antigens associated with autoimmune disorders.

This antigenic similarity between glycine-rich food antigen and Epstein-Barr virus and various tissue antigens involved in autoimmune disease can result in the production of cross-reactive antibodies. The finding of a common peptide epitope able to elicit an immune response in patients with food immune reactivities and different autoimmune disorders gives rise to the question of possible links between food antigens, gut mucosa, and systemic immune response (Lunardi et al., 1992; Schrander et al., 1997). Serum IgG antibodies directed against the GRP peptide were detected in several autoimmune disorders and in food allergic patients, and were able to cross-react with autoantigens including keratin, collagen and EBNA-1 (Lunardi et al., 2000). This data suggests that highly phylogenetically conserved epitopes in plants viruses and humans may be responsible for an autoimmune response in susceptible individuals. Furthermore, this indicates that the antigen spreading of a particular sequence between apparently divergent proteins may be involved in initiating or amplifying an immune response, resulting in autoimmunity in susceptible individuals.

An autoimmune response mediated by T-cell clones specific for particular food antigen epitopes can arise in the gut mucosa. Such T-cells can be recruited to particular sites, such as the joints, where they proliferate in response to homologous peptides derived from synovial proteins. Following local inflammation and up-regulation of MHC molecules, the release of additional self-antigens and/or epitope spreading can lead to a chronic, self-perpetuating process of organ inflammation and destruction resulting in autoimmunity (Lunardi et al., 1992; Vojdani, 2014a).

Recognition of food immune reactivity and associated health problems, particularly in regards to wheat and milk, has grown over the past two decades (Bousquet et al., 1998; Lack, 2008; Zuidmeer et al., 2008). A number of gluten peptides with the capacity to stimulate intestinal T-helper cells have been identified in celiac disease (CD) patients (Arentz-Hansen et al., 2000; Arentz-Hansen et al., 2002; Camarca et al., 2009; Tollefsen et al., 2006). A recent study showed that patients with non-celiac gluten sensitivity (NCGS) and Cohn's disease react to a repertoire of wheat antigens and produce IgG and IgA against them. This repertoire included various peptides, α-, γ-, ω-gliadins, glutenins, gluteomorphins and wheat germ agglutinin (Vojdani, 2011). Continuous exposure to environmental factors such as wheat not only causes NCGS and celiac disease but, if left untreated, can result in inflammation and autoimmunity (Counsell et al., 1994; De Freitas et al., 2002; Gillett et al., 2001). Indeed, celiac disease has been associated with various autoimmune disorders. The spectrum of autoimmune-associated antibodies detected in patients with CD or NCGS indicates that cross-reactivity and molecular mimicry occurs between gliadin and various tissue antigens (Alaedini et al., 2007; Collin et al., 2002; Frustaci et al., 2002; Hadjivassiliou et al., 2004; Jacob et al., 2005; Natter et al., 2001; Pratesi et al., 1998; Reinke et al., 2011; Vojdani et al., 2004).

Many studies have focused on the association between the prevalence of multiple sclerosis (MS) and dairy food consumption, and have found that the incidence of MS parallels the consumption of milk (Agranoff and Goldberg, 1974; Butcher, 1976; Kahana et al., 1994; Knox, 1977; Malosse et al, 1992). Notably, a high degree of sequence homology was found between a major protein of milk fat globule membrane called butyrophilin (BTN) and myelin oligodendrocyte glycoprotein (MOG) (Gardiner et al., 1992; Henry et al., 1999; Jack and Mather, 1990).

MOG (myelin oligodendrocyte glycoprotein) is a major antigen in the pathogenic autoimmune response of MS and its animal model, experimental autoimmune encephalomyelitis (EAE) (Vojdani et al., 2002). MOG is the only myelin autoantigen known to induce both a demyelinating autoantibody response and an ecephalitogenic CD4+ T cell response in animals with EAE (Amor et al., 1994). It has been found that an encephalitogenic T cell response to MOG can be either induced or, alternatively, suppressed as a result of immunological cross-reactivity (or "molecular mimicry") with the extracellular IgV-like domain of the milk protein butyrophilin (BTN). In rats, active immunization with native BTN triggers an inflammatory response in the central nervous system characterized by the formation of scattered meningeal and perivascular infiltrates of T cells and macrophages (Vojdani et al., 2002). It has also been found that this pathology is mediated by an MHC class II-restricted T cell response of BTN that cross-reacts with MOG peptide sequence (Muthukumar M, et al., 2009).

Neuromyelitis optica (NMO) is a severe neuroautoimmune disorder that affects the gray and white matter in the brain and spinal cord, resulting in demyelination, axonal damage, and necrosis, and eventually resulting in paralysis and sensory loss in affected individuals (Jarius et al., 2008). In 75% of cases, NMO is associated with the presence of IgG1 antibody that binds selectively to aquaporin-4 (AQP4), which is a water channel belonging to the aquaporin family (Jarius et al., 2010; Kim et al., 2012). AQP4 is expressed in the astrocytic foot processes at the blood brain barrier, which are in contact with brain microvessels or subarachnoid space affecting solute concentration, electrical activity and modulation of neuronal transmission and excitability (Kinoshita et al., 2010). After binding, AQP4-specific IgG1 antibody has the capacity to first damage the astrocytes, and then cause demyelination in the spinal cord and optic nerve (Bradl and Lassmann, 2008). The binding of IgG1 to AQP4 also induces activation of the complement cascade and inflammatory infiltrates, which, after the induction of astrocytic cytotoxicity, cause demyelination and tissue destruction.

It has recently been suggested that pathogenic antibodies to AQP4 may be triggered by exposure to environmental proteins that have a similarity or molecular mimesis to a specific epitope of AQP4 (Vaishnav et al., 2013). Interestingly, spinach leaves express two thermally stable aquaporins that constitute 20% of the integral membrane protein (Plasencia et al., 2011). Similarly, soybean expresses aquaporins in germinating seeds as well as in the root nodules (Fleurat-Lassard et al., 2005). It has also been found that human AQP4 can cross-react with tomato and corn tonoplast intrinsic proteins (Vaishnav et al., 2013).

It has also been noted that an amino acid sequence with significant identity to a primary T-cell epitope in NMO occurs in a potentially immunogenic coat protein of the Parsnip Yellow Fleck Virus, which infects parsnips, celery, carrots, parsley, cilantro, chervil and dill. This epitope also shares significant sequence identity with a sequence present in a serine-protease inhibitor in the legume M. truncatula (Vaishnav et al., 2013).

It is apparent that many components of foods that have not yet been characterized can also have the potential to trigger autoimmunity. To date most studies associated with food immune reactivity have characterized only the water-soluble population of proteins and peptides present in the studied foods. An exception to this is wheat, as gluten (an alcohol-soluble component of wheat) has been used in food immune reactivity, cross-reactivity, and autoimmunity studies. In addition, the role of complement is not yet clear.

As noted above, to date food allergen studies have focused primarily on the detecting the presence of immunoglobulins to specific antigens, and have not addressed the issue of complement activation. United States Patent Application No. 2009/0010937 (to Chauhan) discusses detection of circulating immune complexes that include complement components such as C1q, however the methodologies that are discussed utilize cellular receptors for immune complexes to provide the immobilization necessary for detection using anti-complement antibodies. As such, they provide little to no insight into the antigen specificity of such complexes. U.S. Pat. No. 8,309,318 (to Dorval and Dantini) discusses the detection of allergen-specific immune complexes containing bound C3b using immobilized antigens. It has been demonstrated, however, that so called "innocent bystander" IgG-C3b adducts can form during complement activation (, which severely limits the utility of such an approach in determining the presence of antigen-specific complexes (Fries et al, 1984).

Thus there is a need for systems, devices, and methods for characterizing antibody (e.g. IgG, IgA, IgM, and other antibody classes) binding to a broader range of antigenic molecules found in food than are represented by water-extractable proteins and peptides in their natural state. In addition, there is a need for systems, devices, and methods that characterize the presence of complement components (e.g. C1q) associated with such antibodies.

SUMMARY OF THE INVENTION

The inventive subject matter provides apparatus, systems and methods in which different groups of antigenic molecules are extracted from foods using a variety of distinct physical/chemical methods, including alkali-soluble proteins, alcohol-soluble proteins, water-soluble proteins, polysaccharides, glycolipids, and glycoproteins. Each of these extracts is applied in a specified order to the same test surface to provide a multiple-coated test surface that includes antigens from each of these different extracts. IgG, IgA, and C1q (in the form of native Immunoglobulin-C1q complexes) that bind to these antigens are identified by exposing the test surface to a sample, washing to remove excess sample, and contacting the exposed test surface with species-specific antibodies to IgG and/or IgA and antibodies to C1q that carry a detectable tag, such as an enzyme. Characterization of the bound tag indicates the degree of IgG, IgA, and/or C1q binding to at least one of the large variety of food antigens present on the test surface.

Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWINGS

FIG. 8 depicts a table showing binding of serum IgG and IgA from an individual to a panel of test surfaces prepared from different foods using commercially available food antigen preparations and test surfaces prepared using methods of the inventive concept. Results are shown for individual antigen preparations for each food, for test surfaces coated sequentially with all food antigen preparations from the food, and for test surfaces coated sequentially with all food antigen preparation derived from the same food after heat treatment.

FIG. 9 depicts a table showing an extension of the food antigen panel shown in FIG. 8.

FIG. 10 depicts a table showing an extension of the food antigen panel shown in FIGS. 8 and 9.

FIG. 11 depicts a table showing an extension of the food antigen panel shown in FIGS. 8, 9, and 10.

DETAILED DESCRIPTION

Figure 1:
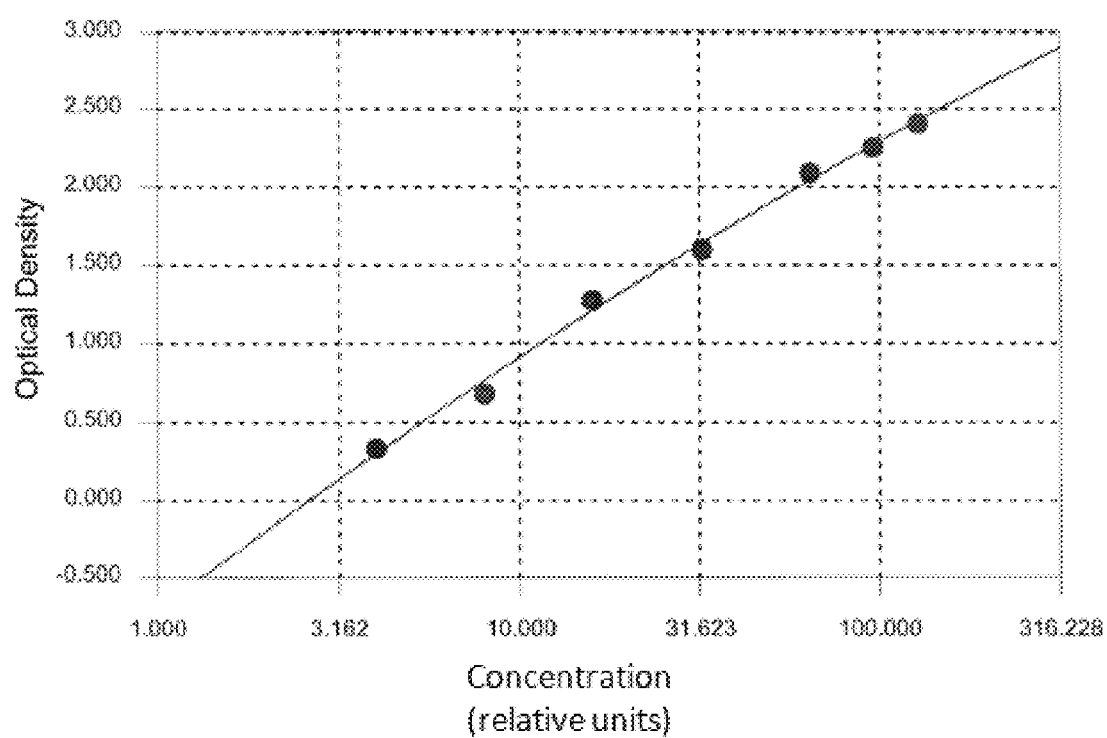
FIG. 1 shows a calibration curve for immune response generated using a test surface of the inventive concept.

Systems, devices, and methods for characterizing the presence of antibodies to food antigens and the presence of C1q-antibody complexes that bind to food antigens are provided. Food antigen extracts are prepared using methods for extraction of water-soluble proteins, alcohol-soluble proteins, alkali-soluble proteins, glycolipids, polysaccharides and glycoproteins from various foods and their heat-denatured versions. When applied to a common test surface in a sequential manner these provide a test surface that provides a far greater variety of food antigens than prior art methods. Surprisingly, the use of sequential addition and the order in which antigen extracts were applied was found to be necessary to produce such composite test surfaces.

In addition, it was found that, when exposed to a plurality of test surfaces each containing food antigen extracts from different food sources, IgG and native Immunoglobulin-C1q complex (i.e. Immunoglobulin-C1q complex formed within an individual) showed different binding profiles. It was also found that characterizing both IgG/IgA and C1q (in the form of native Immunoglobulin-C1q complex) binding simultaneously to the same test surface provided a profile that paralleled results obtained from testing IgG and C1q binding individually, advantageously providing a more complete immunoreactivity profile for food antigens using a reduced number of test surfaces and assay steps.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

Unless the context dictates the contrary, all ranges set forth herein should be interpreted as being inclusive of their endpoints, and open-ended ranges should be interpreted to include only commercially practical values. Similarly, all lists of values should be considered as inclusive of intermediate values unless the context indicates the contrary.

The recitation of ranges of values herein is merely intended to serve as a shorthand method of referring individually to each separate value falling within the range. Unless otherwise indicated herein, each individual value with a range is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

In some embodiments of the inventive concept the food components can be classified into general groups including dairy and eggs (modified), grains (raw and modified), beans and legumes (modified), nuts and seeds (raw and modified), vegetables (raw and modified), fruit (raw and modified), fish and seafood (raw and modified), meat (modified), herbs (raw), spices (raw), gums, and brewed beverages and additives. Modified foods can reflect preparative steps normally carried out prior to consumption, for example boiling, baking, and/or frying.

"Dairy and eggs" can include of egg white, cooked (boiled); egg yolk, cooked (boiled); goat's milk; soft cheese and hard cheese; and yogurt. "Grains, raw and modified" can include rice, white and brown, cooked (boiled); rice cake; rice protein; rice endochitinase; wild rice, cooked (boiled); and wheat+alpha-gliadins.

"Beans and legumes, modified" can include black beans, cooked; bean agglutinins; dark chocolate and cocoa; fava beans, cooked (boiled); garbanzo beans, cooked (boiled); kidney beans, cooked (boiled); lentils, cooked (boiled); lentil lectin, (boiled); lima beans, cooked (boiled); pinto beans, cooked (boiled); soybean agglutinin; soybean oleosin+aquaporin; soy sauce, gluten-free; and tofu.

"Nuts and seeds, raw and modified" can include almonds; almonds, roasted; Brazil nuts, raw and roasted; cashews; cashews, roasted; cashew, vicillin; chia seed; flax seed; hazelnuts, raw and roasted; macadamia nuts, raw and roasted; mustard seed; pecans, raw and roasted; peanuts, roasted; peanut butter; peanut agglutinin; peanut oleosin; pistachios, raw and roasted; pumpkin seeds, roasted; sesame albumin; sesame oleosin; sunflower seeds, roasted; and walnuts.

"Vegetables, raw and modified" can include artichoke, cooked (boiled); asparagus; asparagus, cooked (boiled); beet, cooked (boiled); bell pepper; broccoli; broccoli, cooked (boiled); brussels sprouts, cooked (boiled); cabbage, red+green; cabbage, red+green (boiled); canola oleosin; carrot; carrot, cooked (boiled); cauliflower, cooked (boiled); celery; chili pepper; corn, cooked (boiled); corn aquaporin; popped corn; corn oleosin; cucumber, pickled; eggplant, cooked (boiled); garlic; garlic, cooked (boiled); green bean, cooked (boiled); lettuce; mushroom, raw and cooked (boiled); okra, cooked (boiled); olive, green and black, pickled; onion and/or scallion; onion and/or scallion, cooked (boiled); pea, cooked (boiled); pea protein; pea lectin; potato, white, cooked (baked); potato, white, cooked (fried); pumpkin and/or squash, cooked (baked); radish; safflower and/or sunflower oleosin; seaweed; spinach; spinach aquaporin; tomato; tomato aquaporin; tomato paste; yam and/or sweet potato, cooked (baked); and zucchini, cooked (boiled).

"Fruit, raw and modified" can include apple; apple cider; apricot; avocado; banana; banana, cooked (boiled); latex hevein; blueberry; cantaloupe and/or honeydew melon; cherry; coconut, meat and/or water and/or milk; cranberry; date; fig; grape, red+and green; red wine; white wine; grapefruit; kiwi; lemon and/or lime; mango; orange; orange juice; papaya; peach and/or nectarine; pear; pineapple; pineapple bromelain; plum; pomegranate; strawberry; and watermelon.

"Fish and seafood, raw and modified" can include cod, cooked (baked); halibut, cooked (baked); mackerel, cooked (baked); red snapper, cooked (baked); salmon; salmon, cooked (baked); sardine+anchovy, cooked (boiled); sea bass, cooked (baked); tilapia, cooked (baked); trout, cooked (baked); tuna; tuna, cooked (boiled); whitefish, cooked (baked); crab+lobster, cooked (boiled); imitation crab, cooked (boiled); clam, cooked (boiled); oyster, cooked (boiled); scallops, cooked (boiled); squid (calamari), cooked (boiled); shrimp, cooked (boiled); shrimp tropomyosin; and parvalbumin.

"Meat, modified" can include beef, cooked medium (boiled); chicken, cooked (boiled); lamb, cooked (boiled); pork, cooked (boiled); turkey, cooked (boiled); gelatin; and meat glue (boiled).

"Herbs, raw" can include basil, cilantro, cumin, dill, mint, oregano, parsley, rosemary, and thyme.

"Spices, raw" can include cinnamon, clove, ginger, nutmeg, paprika, turmeric (curcurmin), and vanilla.

"Gums" can include beta-glucan, carrageenan, gum guar, gum tragacanth, locust bean gum, mastic gum+gum arabic, and xantham gum.

"Brewed beverages and additives" can include coffee bean protein, brewed; black tea, brewed; green tea, brewed; honey, raw and processed; and food coloring, artificial.

Prior to extraction foods can be treated to increase the surface area available for extraction processes. For example, food substances can be reduced to particulates by maceration, chopping, grinding, milling, sonication, and/or extrusion. In preferred embodiments of the inventive concept a food to be extracted is initially frozen, for example using liquid nitrogen. The frozen food is then ground or milled, for example using a commercial blender or grinder.

In addition to having utility in reducing food particle size, sonication can also be employed to lyse cells and improve the release of food antigens during extraction. Such sonication can be applied using an ultrasonic bath, by insertion of an ultrasonic horn or probe into the extraction suspension, or by passage through a flow-through sonication device.

A variety of methods are suitable for extracting water soluble proteins (for example, albumins) from foods. Prior to extraction with water or essentially neutral (i.e. pH from 6.5 to 7.5) buffers, the food can be reduced to particulates as noted above. The food can then be suspended in water or an essentially neutral aqueous buffer at a suitable temperature. In some embodiments compounds that inhibit protease activity, such as EDTA, PMSF, and/or pepstatin can be included in the solution used for extraction. In other embodiments surfactants such as 4-(1,1,3,3-tetramethylbutyl)phenyl-polyethylene glycol, polyethylene glycol sorbitan monolaurate, n-dodecyl-$\beta$-D-maltoside, alkyphenol ethoxylate, and sodium dodecyl sulfate, can be included in the solution used for extraction. Suitable extraction temperatures can range from 4° C. to 95° C., as is appropriate for the particular food being treated. Similarly, the time required for optimal extraction can depend upon the food, the particle size, and the nature of the water-extractable protein antigens. Suitable extraction times can range from 30 minutes to 48 hours. Following extraction residual solids can be removed by settling and decantation, centrifugation, filtration, or a combination of these. Following extraction and removal of extracted solids, the water soluble protein antigen preparation can be transferred to a suitable binding buffer, or, alternatively, can be stored prior to use. Water soluble protein antigen preparations can be lyophilized for storage, stored in liquid form at reduced temperature, or stored frozen prior to use. In some embodiments an additive, such as glycerol, can be added to the water soluble protein antigen preparation to permit liquid storage at temperatures of less than 0° C.

A variety of methods are suitable for extracting alkali soluble proteins) from foods. Prior to extraction with alkaline solution, the food can be reduced to particulates as noted above. The food can then be suspended in a basic (i.e. pH greater than or equal to about 8) solution at a suitable temperature. In preferred embodiments of the inventive concept such an alkaline solution can have a pH greater than or equal to about 10. Such alkaline solutions can be prepared by adding basic salts to water. Suitable basic salts include $NaOH$, $KOH$, $Ca(OH)_2$, $Na_2CO_3$, $NaHCO_3$, $Na_2HPO_4$, $K_2CO_3$, $KHCO_3$, $Ca(HCO_3)_2$, $CaCO_3$, and combinations thereof. Alternatively, suitable alkaline buffers can be prepared using buffers such as CAPS, CAPSO, Tris, and/or glycine. In other embodiments of the inventive concept such an alkaline solution can have a pH greater than or equal to about 9. In some embodiments of the inventive concept such an alkaline solution can have a pH greater than or equal to 8. In some embodiments compounds that inhibit protease activity, such as EDTA, PMSF, and/or pepstatin can be included in the alkaline solution used for extraction. In other embodiments surfactants such as 4-(1,1,3,3-tetramethylbutyl)phenyl-polyethylene glycol, polyethylene glycol sorbitan monolaurate, and sodium dodecyl sulfate, can be included in the alkaline solution used for extraction. Suitable extraction temperatures can range from 4° C. to 95° C., as is appropriate for the particular food being treated. Similarly, the time required for optimal extraction can depend upon the food, the particle size, and the nature of the alkaline-extractable protein antigens. Suitable extraction times can range from 30 minutes to 48 hours. Following extraction residual solids can be removed by settling and decantation, centrifugation, filtration, or a combination of these. Following extraction and removal of extracted solids, the alkaline soluble protein antigen preparation can be transferred to a suitable binding buffer, or, alternatively, can be stored prior to use. Alkaline soluble protein antigen preparations can be lyophilized for storage, stored in liquid form at reduced temperature, or stored frozen prior to use. In some embodiments an additive, such as glycerol, can be added to the water soluble protein antigen preparation to permit liquid storage at temperatures of less than 0° C.

A variety of methods are suitable for extracting alcohol/organic soluble proteins from foods. Prior to extraction with an alcohol or other organic solvent, the food can be reduced to particulates as noted above. The food can then be suspended in an aqueous solution of alcohol or other suitable organic solvent. Suitable alcohols include methanol, ethanol, propanol, and mixtures thereof. Other suitable organic solvents are at least miscible with water, and include DMSO, DMF, and glycerol. Suitable extraction temperatures can range from 4° C. to 95° C., as is appropriate for the particular food being treated. Similarly, the time required for optimal extraction can depend upon the food, the particle size, and the nature of the water-extractable protein antigens. Suitable extraction times can range from 30 minutes to 48 hours. Following extraction residual solids can be removed by settling and decantation, centrifugation, filtration, or a combination of these. Following extraction and removal of extracted solids, the alcohol/organic soluble protein antigen preparation can be transferred to a suitable binding buffer, or, alternatively, can be stored prior to use. Alcohol/organic soluble protein antigen preparations can be lyophilized for storage, stored in liquid form at reduced temperature, or stored frozen prior to use. In some embodiments an additive, such as glycerol, can be added to the water soluble protein antigen preparation to permit liquid storage at temperatures of less than 0° C.

A variety of methods are suitable for extracting glycolipids from foods. Prior to extraction, the food can be reduced to particulates as noted above. A lipid containing fraction can be extracted from the food using an organic solvent or organic solvent mixture, such as chloroform, methanol, pyridine, or a mixture thereof. Glycolipids can be separated from the extracted lipid mixture using ion exchange chromatography, for example using a DEAE substituted chromatography media, and eluted with an organic solvent/aqueous salt solution mixture (such as sodium acetate mixed with a chloroform/methanol mixture). In some embodiments sonication can be applied during this extraction. In some embodiments the eluted glycolipids can be hydrolyzed using a basic solution, then neutralized. The resulting salts can be removed by a suitable desalting process, such as gel filtration, hydrophobic interaction chromatography, and/or reverse phase chromatography. Suitable extraction temperatures can range from 4° C. to 95° C., as is appropriate for the particular food being treated. Similarly, the time required for optimal extraction can depend upon the food and the particle size. Suitable extraction times can range from 30 minutes to 48 hours. Following extraction residual solids can be removed by settling and decantation, centrifugation, filtration, or a combination of these. Following extraction and removal of extracted solids, the glycolipid antigen preparation can be transferred to a suitable binding buffer, or, alternatively, can be stored prior to use. Glycolipids can be evaporated to dryness, lyophilized, stored in liquid form at reduced temperature, or stored frozen prior to use. In some embodiments an additive, such as glycerol, can be added to the glycolipid preparation to permit liquid storage at temperatures of less than 0° C.

A variety of methods are suitable for extracting polysaccharides from foods. Prior to extraction, the food can be reduced to particulates as noted above. A polysaccharide containing fraction can be extracted from the food by enzymatic digestion, for example using cellulase. Following a suitable period of time enzymatic activity can be halted, for example by boiling the extraction mixture. Following this, proteins (including the added enzyme) can be removed from the polysaccharide antigen preparation by precipitation. Proteins can be conveniently precipitated using a volatile organic solvent such as chloroform, butanol, or mixtures thereof. Suitable extraction temperatures can range from 4° C. to 100° C., as is appropriate for the particular food being treated. Similarly, the time required for optimal extraction can depend upon the food and the particle size. Suitable extraction times can range from 30 minutes to 48 hours. Following extraction residual solids can be removed by settling and decantation, centrifugation, filtration, or a combination of these. Following extraction and removal of extracted solids, the polysaccharide antigen preparation can be transferred to a suitable binding buffer, or, alternatively, can be stored prior to use. Polysaccharides can be evaporated to dryness, lyophilized, stored in liquid form at reduced temperature, or stored frozen prior to use. In some embodiments an additive, such as glycerol, can be added to the polysaccharide preparation to permit liquid storage at temperatures of less than 0° C.

Glycoprotein antigens, which for the purposes of this application are understood to be proteins that have an affinity for sugars, can be extracted from foods by a variety of methods. Prior to extraction, the food can be reduced to particulates as noted above. A glycoprotein containing fraction can be extracted from the food by, for example, affinity chromatography or specific precipitating agents. In affinity chromatography methods, a protein fraction obtained from the food is applied to a chromatographic media that includes fixed saccharide or polysaccharide groups capable of interacting with the glycoprotein. Bound glycoproteins can be subsequently eluted from the media by applying a solution of an appropriate sugar, such as glucose, galactose, mannose, or derivatives thereof. Specific precipitating agents can include compounds that include sugar moiety and poorly-soluble organic moiety. Binding of such compounds can cause glycoproteins to precipitate under the proper buffer conditions (for example, in the presence of divalent cations). Such precipitated glycoproteins can be recovered by, for example, cleaving the precipitating reagent to release the poorly-soluble organic moiety followed by a desalting step (several examples of which are provided above). Suitable extraction temperatures can range from 4° C. to 95° C., as is appropriate for the particular food being treated. Similarly, the time required for optimal extraction can depend upon the food and the particle size. Suitable extraction times can range from 30 minutes to 48 hours. Following extraction residual solids can be removed by settling and decantation, centrifugation, filtration, or a combination of these. Following extraction and removal of extracted solids, the glycoprotein antigen preparation can be transferred to a suitable binding buffer, or, alternatively, can be stored prior to use. Glycoproteins can be lyophilized, stored in liquid form at reduced temperature, or stored frozen prior to use. In some embodiments an additive, such as glycerol, can be added to the glycoprotein preparation to permit liquid storage at temperatures of less than 0° C.

As noted above, in some embodiments it is desirable to transfer an extracted antigen preparation from one buffer to another, for example from one processing buffer to another or from a storage buffer to a buffer suitable for attaching the antigen to a solid phase. Such a buffer transfer can be accomplished by dialysis against the new buffer using a dialysis membrane with an exclusion limit that retains the extracted antigen. Alternatively, buffers can be changed using size exclusion chromatography over appropriate chromatography media. In still other embodiments, buffers can be exchanged by precipitation using a volatile additive, collection and drying of the precipitate, and resolubilization in the desired buffer.

In order to be used in an antibody and/or C1q binding assay, extracted antigens are coupled to a solid phase. Within the context of this application the term "solid phase" includes insoluble, suspended phases such as particles and microparticles. Such microparticles can be encoded, for example by particle size and/or the incorporation of dyes, to permit differentiation of particle populations (for example, particles associated with antigens derived from a particular food). Such encoding can permit simultaneous determinations within a single, multiplexed assay. Typical solid phases include, but are not limited to, microwell plates, microwell strips, microarrays, porous or fibrous materials, pipette tips, beads, and microparticles. Such coupling can be covalent (i.e. utilizing covalent bonds between molecules of the extracted antigen and the solid phase) or non-covalent. In a preferred embodiment of the inventive concept, the solid phase is at least a portion of the internal surface of a well of a microwell plate or microwell strip. Such microwells can be constructed of any suitable material, including polystyrene, polycarbonate, polypropylene, and polyethylene. In some embodiments of the inventive concept the microwell surface has been chemically or physically modified (for example, by texturing) to enhance binding.

Assays utilized to detect the formation of complexes between antibody and/or C1q from a sample and an immobilized food antigen can be immunoassays. Such immunoassays can be indirect (i.e. competitive) or direct (i.e. "sandwich" assays), and can utilize any suitable detectable label (for example, fluorescent moieties, chromogenic moieties, mass labels, radioactive moieties, and/or enzymes). In a preferred embodiment of the inventive concept, the assay is a direct immunoassay utilizing an enzyme label such as alkaline phosphatase or horseradish peroxidase. It should be appreciated that, while more than one specific antibody (for example, anti-species IgG, anti-species IgA, and/or anti-C1q) may be applied to a single test surface that a common label can be used for all.

In some embodiments of the inventive concept, antigens from antigen preparations as described above are affixed to a solid test surface by adsorption. A test surface of the inventive concept includes antigens obtained from at least two different antigen extracts, prepared from a single food source by different methods. In some embodiments the test surface includes at least three different antigen extracts, prepared from a single food source by different methods. In other embodiments the test surface includes at least four different antigen extracts, prepared from a single food source by different methods. In still other embodiments the test surface includes at least five different antigen extracts, prepared from a single food source by different methods. In preferred embodiments the test surface includes at least six different antigen extracts, prepared from a single food source by different methods.

In a preferred embodiment of the inventive concept, antigen preparations prepared as described above are adsorbed to a test surface in a sequential stepwise manner, with unbound material removed between additions. For example, an antigen preparation prepared from a food can be applied to a test surface for a period of time sufficient to permit adsorption. Such periods of time can range from 0.5 to 48 hours, and can be performed at temperatures range from 4° C. to 50° C. Unbound material is then removed, for example by pipetting, prior to adsorption of a second, different antigen preparation derived from the same food. Optionally, the test surface can be washed prior to contacting it with a second and/or subsequent antigen preparation. Such washing can be performed using a wash buffer, which can include a surfactant. Suitable surfactants include polyoxyethylene sorbitan monolaurate (Tween 20), polyoxyethylene sorbitan monooleate (Tween 80), 4-(1,1,3,3-tetramethylbutyl)phenyl-polyethylene glycol (Triton X-100), and/or octylphenoxy poly(ethyleneoxy)ethanol (Nonidet P40). This process can be repeated with additional (for example, third, fourth, fifth, and or sixth) food antigen preparations from the same food to produce a sequentially coated test surface.

Surprisingly despite prior exposure to antigen preparations and to surfactant-containing wash buffers, many common test surfaces (for example polystyrene microwells) have been found to retain the capacity to adsorb additional antigenic material. Following the application of the final antigen preparation, remaining adsorption sites of the test surface can be blocked by application of a blocking buffer. Such blocking buffers can contain one or more proteins (i.e. blocking proteins) that occupy residual adsorption or coupling sites of the test surface but do not provide significant interaction with other assay components. Examples of suitable blocking proteins include serum albumins, ovalbumins, gelatin, milk proteins, and nonspecific immunoglobulins from suitable species.

Surprisingly, the inventors have found that test surfaces including multiple antigen extracts could not be effectively produced by mixing such antigen extracts prior to application to the test surface. Such mixture proved to be unstable, resulting in the formation of precipitates that removed at least some antigenic compounds prior to application to the test surface. Since the loss of such antigens can result in a false negative result for that particular food, this is highly undesirable. Surprisingly, the inventors have found that applying food antigen preparations to a test surface sequentially generates a test surface in which a broader variety of food antigens is present. In some embodiments of the inventive concept the food antigens preparations are added in a specific order. For example, multiple food antigen preparations can be applied in the following order successfully: first alkali soluble proteins, then alcohol soluble proteins, then water soluble proteins, then polysaccharides, then glycolipids, and finally glycoproteins. In other embodiments of the inventive concept, a different order of addition can be suitable provided that the different antigen preparations are applied to the test surface in separate, distinct steps. It should also be appreciated that in some embodiments one or more of the food antigen preparations discussed above can be omitted from the coating process.

EXAMPLES

Example 1

Extraction of Proteins from Various Foods

Suitable methods for extraction of water-soluble, alcohol-soluble, and alkaline-soluble proteins from various food sources are as follows:

Step 1—For each protein antigen preparation, grind or mill 2 grams of dry beans, nuts, seeds and spices or 20 grams of wet fruits or vegetables in one of three different solvents/buffers (designated A, B, and C):
  A. 100 mL of 0.1 M PBS (pH 7.2) for water-soluble proteins
  B. 100 mL of 70% ethanol for alcohol soluble proteins
  C. 100 mL of 0.1 M KOH (pH 10.0) for alkali soluble proteins.

Step 2—Apply 2 to 5 minutes of sonication in order to lyse the cells. Add 2 mL of detergent (1,1,3,3-tetramethylbutyl)phenyl-polyethylene glycol or n-dodecyl-β-D-maltoside) and repeat the sonication for an additional 2-5 minutes.

Step 3—Stir the mixture for 2 hours, and then centrifuge each preparation at 10,000 g for 15 minutes. Remove the supernatant.

Step 4—Transfer each supernatant to a separate dialysis bag (6,000 dalton MW cutoff) and dialyze against a specific solvent. For example, for a solution of protein antigen dissolved in PBS, dialysis should be performed against PBS. Similarly, for a protein antigen extracted with KOH, dialysis should be performed against 0.1 M KOH.

Step 5—After 48 hours of dialysis, collect the dialyzed solutions and centrifuge at 14,000 g for 15 minutes. Samples can be removed for measurement of protein concentration; remaining protein antigen preparations can be stored at −20° C. until needed for use in immunological assays.

Example 2

Extraction of Glycolipids from Various Foods

A suitable method for extraction of glycolipids from various food sources is as follows.
  Step 1—Grind or mill 2 grams of dry beans, nuts, seeds and spices or 20 grams of wet fruits or vegetables in 100 mL of water.
  Step 2—Apply 2 to 5 minutes of sonication to lyse the cells.
  Step 3—Add 120 mL of chloroform:methanol (2:1, v:v) and repeat the sonication.
  Step 4—Add 600 µl of pyridine and incubate the mixture at 50° C. for 24 hours to extract simple lipids, phospholipids and glycolipids.
  Step 5—Apply the chloroform:methanol extract to a DEAE-based ion exchange media; then elute the glycolipids from the column with chloroform:methanol: sodium acetate (1:2:1, v:v:v).
  Step 6—Hydrolyze the eluted glycolipids with a 0.1 N sodium hydroxide/methanol solution, neutralize using acetic acid, then desalt by binding to and subsequent elution from a C-18 reverse phase column.
  Step 7—Dissolve the desalted glycolipids in chloroform: methanol (2:1, v:v).
  Step 8—Remove the organic solvents from the dissolved glycolipid at 55° C. using a rotary evaporator. This dried material can be stored at −20° C.
  Step 9—To use, suspend the glycolipids in 70% methanol and sonicate for 2 minutes at room temperature.

Example 3

Preparation of Polysaccharides from Various Foods

A suitable method for producing polysaccharides from fruits, vegetables, or beans, is as follows.
  Step 1—Grind or mill 2 grams of dry beans, nuts, seeds and spices or 20 grams of wet fruits or vegetables in 100 mL of water.
  Step 2—Apply 2 to 5 minutes of sonication in order to lyse the cells.
  Step 3—Add 100 mg of cellulase and incubate at 37° C. for 4 hours.
  Step 4—Increase the temperature to 100° C. and incubate for 60 minutes.
  Step 5—Centrifuge at 10,000 g for 15 minutes and retain the supernatant.
  Step 6—Add 4:1 chloroform:butyl alcohol (4:1, v:v) to remove free proteins, including cellulase.
  Step 7—Precipitate polysaccharides from deproteinated solution by adding 4 volumes of 95% ethanol, then re-dissolve the precipitate in 100 mL of water.
  Step 8—Determine the neutral sugar content (for example, by the phenol-sulfuric acid colorimetric method of Dubois et al, 1956) using glucose as a standard, and further characterize monosaccharide composition (for example, by the method of Sheng et al 2007). Polysaccharide preparations can be stored at −20° C. until needed for use in immunological assays.

Example 4

Extraction of Glycoproteins from Various Foods

A suitable method for extraction of glycoproteins from various food sources is as follows.
  Step 1—Grind or mill 100 grams of fruits, vegetables, beans, legumes, nuts, seeds, spices, herbs, dairy, eggs, meat, seafood, gum or beverages in a blender.
  Step 2—Add 100 mL of 2% (w/v) $CaCl_2$ and homogenize for 5 minutes.
  Step 3—Apply 3 minutes of sonication in order to lyse the cells.
  Step 4—Stir the mixture for 2 hours at room temperature, and then centrifuge the solution at 10,000 g for 30 minutes. Retain the supernatant.
  Step 5—Add 120 mL of 2% (w/v) $CaCl_2$ containing 120 mg of 1,3,5-P-β-D-galactosyl-oxyphenazo) 2,4,6-trihydroxybenzene and stir for 1 hour in order to precipitate the glycoproteins.
  Step 6—Collect the precipitate containing glycoproteins by centrifuging for 10 minutes at 2,000 g.
  Step 7—Dissolve the precipitate in 15 mL of distilled water.
  Step 8—Add 250 mg of sodium metabisulphite dissolved in 5 mL of distilled water to reduce the diazo linkage.

Step 9—Cap the tube containing the glycoproteins tightly and incubate at 50° C. for 20 minutes.

Step 10—Dialyze the reduced glycoprotein solution against 3 liters of distilled water using a dialysis membrane with a molecular weight cutoff for 3 days, changing the water daily.

Step 11—Centrifuge the dialyzed material at 14,000 g for 15 minutes. Glycoprotein concentration can measured using the DIG GLYCAN DETECTION KIT® from Roche Life Sciences (Indianapolis, Ind.). The preparation can be stored at −20° C. until used in immunological assays.

Example 5

Binding of Various Food Extracts to a Solid Matrix for Measurement of Antibodies In successful plate coating using the antigen preparations extracted as described above to the same test surface, different extracts are added sequentially to the same test surface, with wash steps provided between successive additions to remove unbound materials. A suitable order for addition to the wells of a microwell plate is as follows.

Step 1—Add alkali-soluble proteins to the plate, followed by 24 hours of incubation at 4° C. and then washing with PBS/Tween 20.

Step 2—Add alcohol-soluble proteins to the plate, followed by 24 hours of incubation at 4° C. and then washing with PBS/Tween 20.

Step 3—Add water-soluble proteins to the plate, followed by 24 hours of incubation at 4° C. and then washing with PBS/Tween 20.

Step 4—Add polysaccharides to the plate, followed by 24 hours of incubation at 4° C. and then washing with PBS/Tween 20.

Step 5—Add glycolipids to the plate, followed by 24 hours of incubation at 4° C. and then washing with PBS/Tween 20.

Step 6—Add glycoproteins to the plate, followed by 24 hours of incubation at 4° C. and then washing with PBS/Tween 20.

Step 7—After all six antigen preparationss have been added to the plate and the antigens contained therein allowed to bind to the solid matrix, saturate the remaining non-specific binding sites are saturated by adding with 2% (w/v) bovine serum albumin, 2% (w/v) ovalbumin, 2% (w/v) dry milk, 2% (w/v) gelatin, or 2% (w/v) teleost gelatin. After a final washing with PBS/Tween 20 the plate can be stored at 4° C. until used for antibody and/or C1q measurement.

Example 6

Assay Procedure for Detection of IgG, IgA Antibodies and Immunoglobulin-C1q Complex in Blood Against a Combination of Extracts of Various Foods The following procedure describes the use of microwell plates coated with the combination of food extracts according to Example 5. It should be appreciated that test tubes, nitrocellulose paper, microparticle suspensions, and other matrices could be used.

Serum samples were collected from individuals by venipunture and allowed to rest for 20 minutes at room temperature. Other sample types are also suitable, including plasma, whole blood, saliva, mucus, synovial fluid, and/or cerebrospinal fluid. After centrifugation for 10 minutes at 800 g the serum was removed and stored at −40° C.

Wash buffer was prepared as follows: in a 500 mL graduated cylinder, 450 mL of water was added to 50 mL of 10× wash buffer (1.0 L 1×PBS diluted with 3.0 L distilled or deionized $H_2O$; 1.5 mL of Tween 20; 400 mg sodium azide). The solution was mixed and transferred to a 500 mL squeeze bottle and stored at 2-8° C. until used.

Anti-immunoglobulin and anti-C1q antibodies were prepared as follows: 100 µl of enzyme-labeled anti-human IgG, anti-human IgA, anti-human IgG plus anti-C1q complement, or anti-human IgA plus anti-C1q complement were added to 20-50 mL of a conjugate diluent containing 0.1 M PBS/Tween 20 and 2% BSA, and used for the detection of antibodies and/or C1q antibody conjugates in the sera.

Substrate solution was prepared immediately prior to use by adding 5 mL of substrate buffer per 5 mg substrate tablet in an empty polypropylene tube. The tube was capped, mixed to dissolve the tablet, and then the solution was used immediately. Approximately 1 mL of substrate solution was used per microwell strip.

For antibody and C1q profile characterization, serum was diluted 1:100 (v/v) by the addition of 40 µl of serum to 4 mL of a diluent buffer containing 0.1 M PBS/Tween 20 plus 2% BSA.]. It should be appreciated that this dilution can be adapted as necessary, and can range from 1:20 (v/v) to 1:400 (v/v). The diluted serum is added to duplicate wells prepared for each food and incubated for 30 to 60 minutes at 4° C. to 25° C. This incubation can be a short as 15 minutes and as long as 24 hours. After incubation, the plates are washed 3-6 times using wash buffer such as 0.1 M PBS/Tween 20, then 100 µl of appropriately diluted anti-human IgG, anti-human IgA or anti-human IgG plus anti-human C1q, all labeled with an enzyme such as alkaline phosphatase, are added to the tested wells. Suitable dilutions for such anti-immunoglobulin and anti-C1q conjugates can range from about 1:200 to about 1:1000 (v/v).

The microwell plates or strips are then covered and incubated for 60 minutes at room temperature (i.e. 22° C. to 25° C.). The liquid is then removed from all the wells and the wells washed four times with about 200 µL of wash buffer. 100 µl of p-NPP substrate solution is then added to the wells at timed intervals that corresponded to the reading time of the instrument used to read the reactions (for example, if the instrument requires 30 seconds to acquire the data from a single well, the substrate is added to the wells at 30 second intervals). The incubation time of the substrate in each well is from 45 minutes to 60 minutes, at a temperature of 22° C. to 25° C. It should be appreciated that this time can be reduced if the substrate incubation step is performed at higher temperatures. The enzymatic reaction is stopped by adding 50 µl of 3N NaOH to the wells at the same timed intervals at which the p-NPP was added. The microwell plate is then shaken for 1 to 2 minutes. The bottom of the microwell plate is blotted with a non-abrasive paper towel prior to reading, and the instrument is zeroed on a blank well. The optical density (OD) was read at 405 nm±5 nm within 30 minutes of stopping the enzymatic reaction and the value recorded.

The titer or antibody level can be determined with a computer-implemented program using the following formulas:

IgG, IgA or IgG+C1q Index=(Absorbance of test specimen)/(Absorbance of calibrator)   1)

IgG, IgA or IgG+C1q Level=((Values of calibrators)×(Absorbance of test specimen))/(Absorbance of calibrators)      2)

For precise determination, absorbances can be converted to concentration values using a point-to-point data reduction method. Alternatively, a best-fit linear regression can be used to obtain values.

The values were obtained using an automated ELISA reader. The X-axis was each calibrator's concentration value. The Y-axis was the corresponding mean absorbance value expressed as optical density (OD). A best-fit line was derived. The concentration of each patient's saliva or serum was obtained by locating its absorbance on the Y-axis and finding the corresponding concentration value on the X-axis. An example of a typical calibration curve is shown in FIG. 1. Concentration is expressed in relative units, which in practice are dependent upon the nature of the calibrating species.

Figure 2:
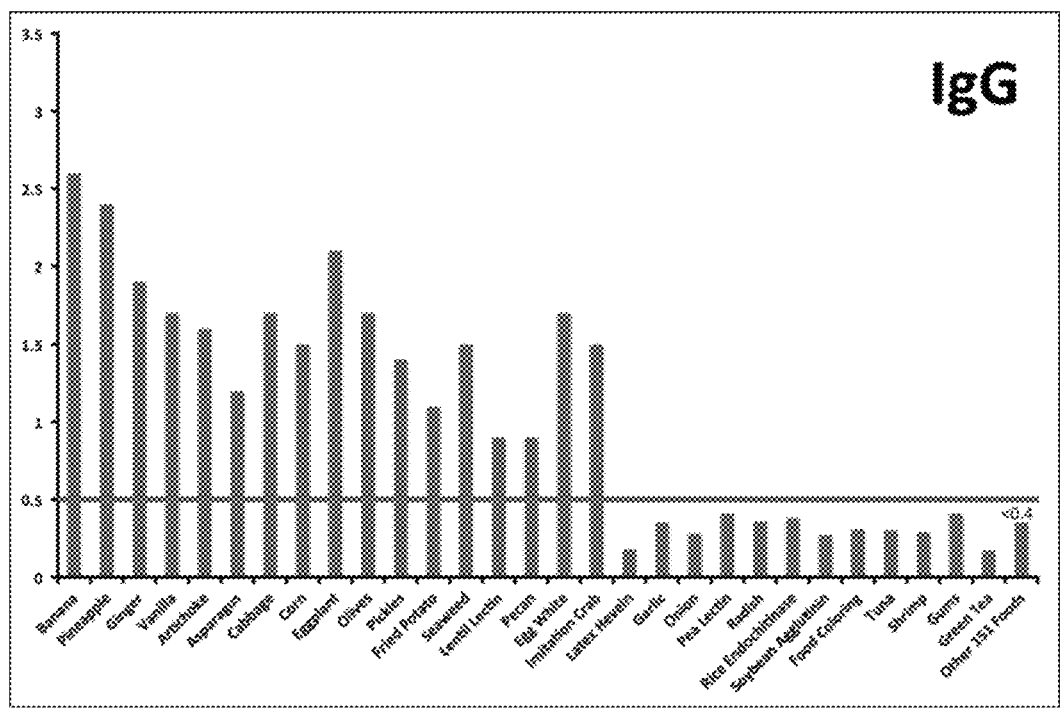
FIG. 2 shows results of IgG binding studies to a test surface of the inventive concept. IgG antibody binding was characterized using test surfaces that included different antigen-containing extracts from 180 tested foods for a first individual. Results above the assay cutoff of 0.5 OD indicate a significant elevation in IgG against banana, pineapple, ginger, vanilla, artichoke, asparagus, cabbage, corn, eggplant, olives, pickles, fried potato, seaweed, lentil lectin, pecan, egg white and imitation crab. IgG immune reactivity against the remaining 163 food extracts was below 0.4 OD and was considered negative.

Results obtained using serum obtained from a first patient are shown in FIG. 2. FIG. 2 shows IgG antibody elevation against antigens prepared from 180 tested foods, characterized using well of microwell plates sequentially coated as described above, and probed only with anti-human IgG. A cutoff optical density value of 0.5 O.D. was selected based on the distribution of non-elevated values, with optical density above this value being indicative of a positive response. Note in this example with a cutoff of 0.5 that significant elevation is observed against banana, pineapple, ginger, vanilla, artichoke, asparagus, cabbage, corn, eggplant, olives, pickles, fried potato, seaweed, lentil lectin, pecan, egg white and imitation crab. IgG immune reactivity against the other 163 food extracts was below the 0.5 OD or negative.

Figure 3:
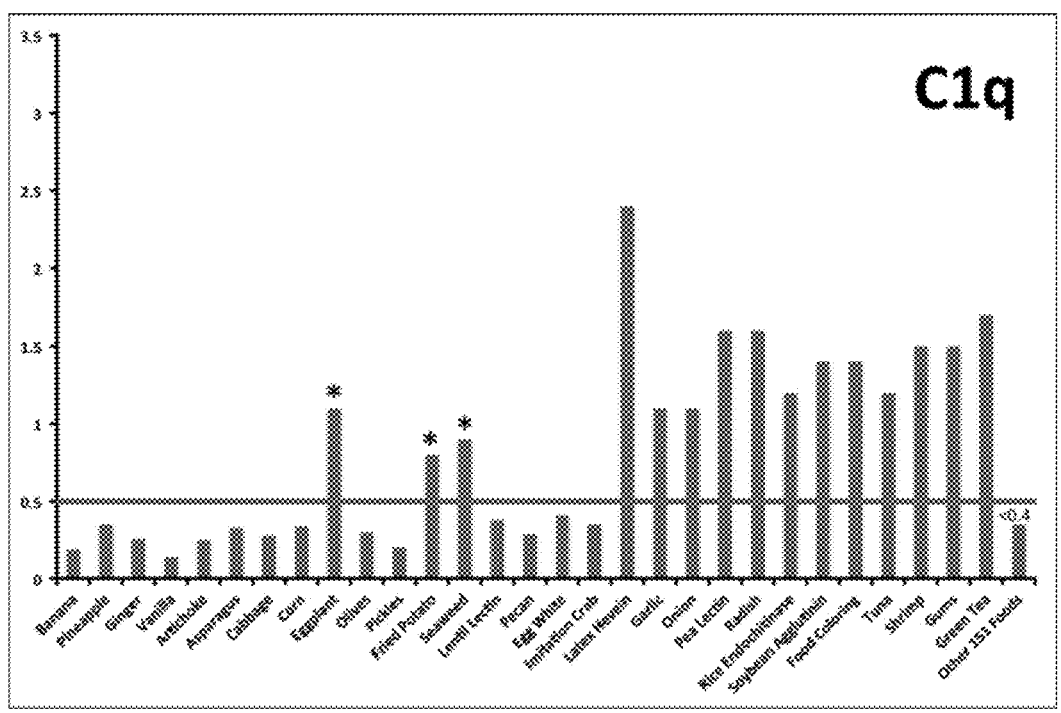
FIG. 3 shows the results of assays for C1q binding (via native Immunoglobulin-C1q complex) to a test surface of the inventive concept. Immunoglobulin-C1q binding was characterized using test surfaces that included different antigen-containing extracts from 180 tested foods for a first individual. Note in the example that when C1q binding (via native Immunoglobulin-C1q complex) is measured, the level of this complex is significantly elevated against 12 different new food extracts that were not positive when IgG was measured. These extracts are latex hevein, garlic, onion, pea lectin, radish, rice endochitinase, food coloring, tuna, shrimp, gums and green tea. It is also notable that when the level of IgG was measured as shown in FIG. 2, the optical densities for these same 12 foods were below 0.5 and was considered negative.

Results for the same sample, but where the wells of the microwell plate were probed only with anti-C1q antibody, are shown in FIG. 3. FIG. 3 shows the elevation in the level of C1q binding (in the form of native Immunoglobulin-C1q complex) to antigen mixtures prepared from 180 tested foods. Note c1q is measured in this fashion the concentration of this complex is significantly elevated against 12 different new food extracts that were not positive when only IgG was measured. These extracts are latex hevein, garlic, onion, pea lectin, radish, rice endochitinase, food coloring, tuna, shrimp, gums and green tea. Furthermore, note that for these 12 foods the concentration of IgG was below 0.5 or negative when similar wells were probed with anti-human IgG (see FIG. 2).

Figure 4:
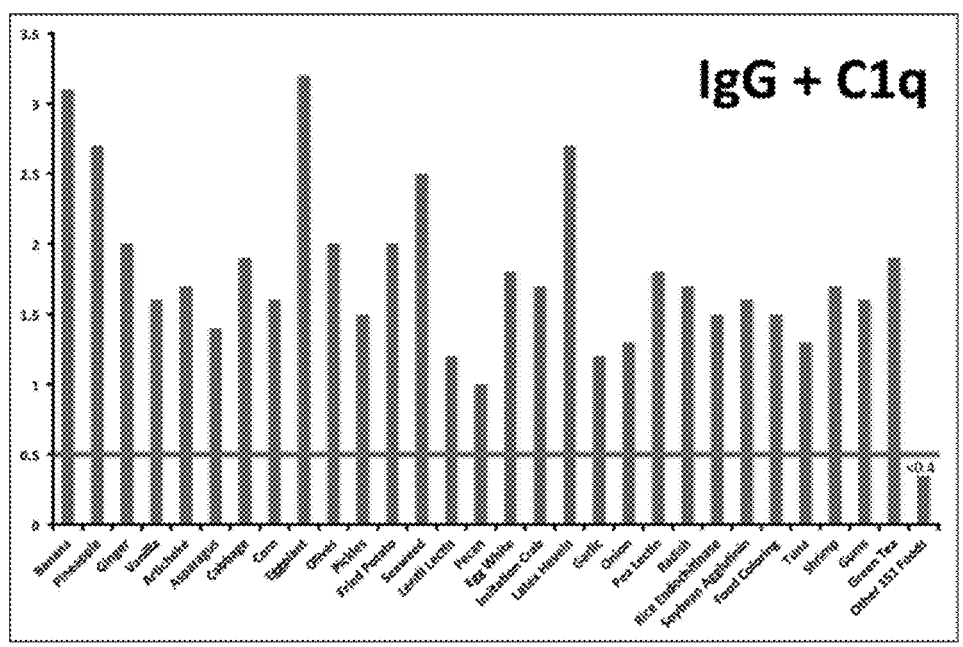
FIG. 4 shows the results of assays for both IgG and C1q binding (via native Immunoglobulin-C1q complex to the same test surface of the inventive concept. IgG and C1q binding were characterized using test surfaces that included different antigen-containing extracts from 180 tested foods for a first individual. All food extracts which were reactive when either IgG or C1q was measured (as shown in FIGS. 2 and 3) became highly reactive. For the remaining 151 foods the optical densities were below 0.5 and considered negative.

Results for the same sample, but where each of the wells of the microwell plate were probed only with both anti-human IgG and with anti-C1q antibody, are shown in FIG. 4. FIG. 4 shows that when the combination of IgG and C1q-IgG complex was measured by simultaneously applying both anti-human IgG and anti-human C1q, all food extracts which were reactive when either IgG or C1q-IgG was measured (as shown in FIGS. 2 and 3) became highly reactive. For the other 151 foods the optical densities were below 0.5 or negative.

These findings demonstrate that if only IgG antibody binding had been characterized for the serum of this individual, then reactivity against only the 17 food extracts would have been detected. Similarly, if only native Immunoglobulin-C1q complex is measured, the patient's C1q profile shows a reaction to 12 food extracts which were not detected by IgG measurement alone. When both IgG and C1q-IgG are measured simultaneously, however, a profile showing reactivity to all 29 food extracts is generated (shown in FIG. 4), combining both the 17 detected by IgG (shown in FIG. 2) and the additional 12 detected by C1q-IgG evaluation (shown in FIG. 3).

Figure 5:
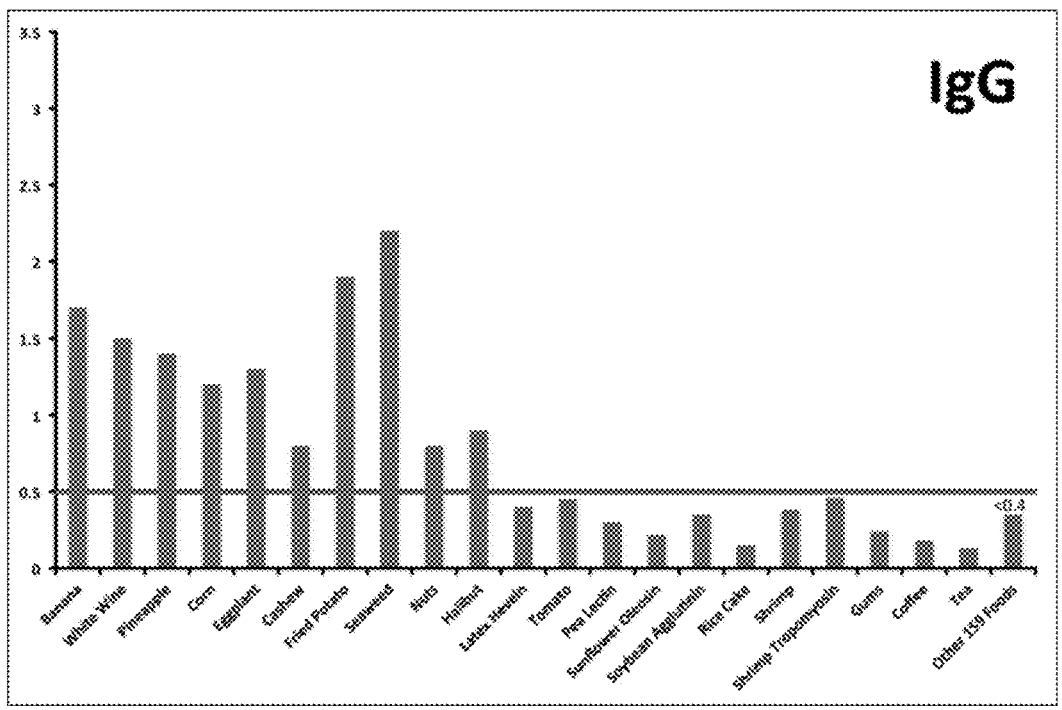
FIG. 5 shows results of IgG binding studies to a test surface of the inventive concept. IgG antibody binding was characterized using test surfaces that included different antigen-containing extracts from 180 tested foods for a second individual. Results above the assay cutoff of 0.5 OD indicate a significant elevation in IgG. Significant IgG binding to 10 out of 180 food antigen extracts was identified.
Figure 6:
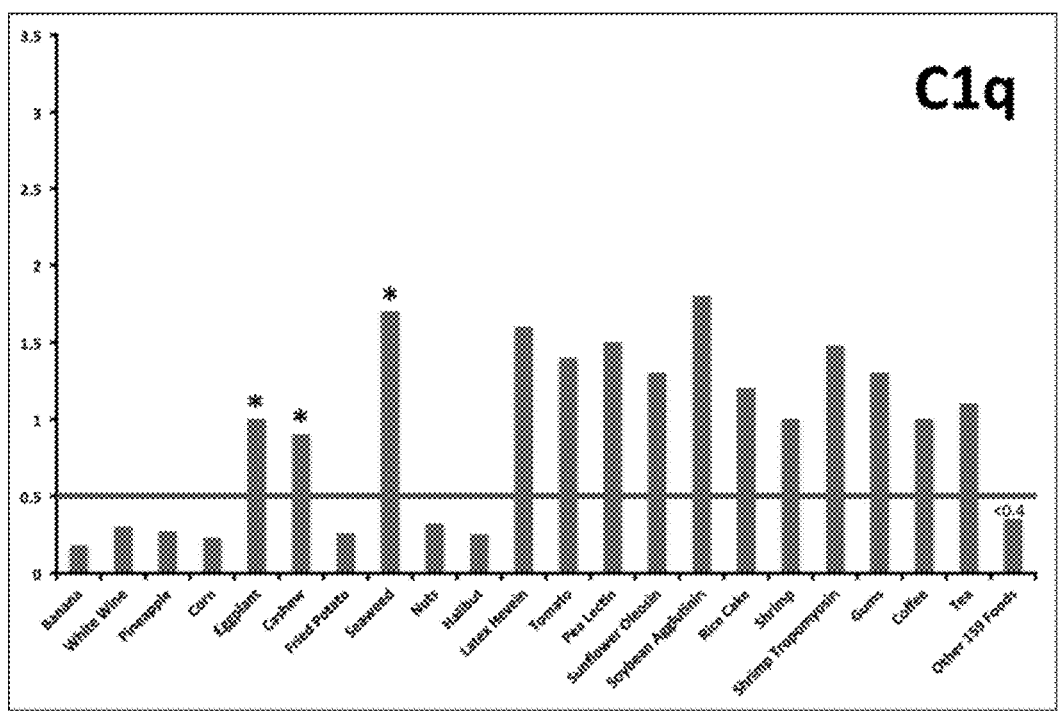
FIG. 6 shows the results of assays for C1q binding (via native Immunoglobulin-C1q complex) from the second individual to a test surface of the inventive concept. C1q binding was characterized using test surfaces that included different antigen-containing extracts from 180 tested foods. Results above the assay cutoff of 0.5 OD indicate a significant elevation in C1q. Significant C1q binding (via native Immunoglobulin-C1q complex) was identified for 14 food antigen extracts, 11 of which were unique to C1q.
Figure 7:
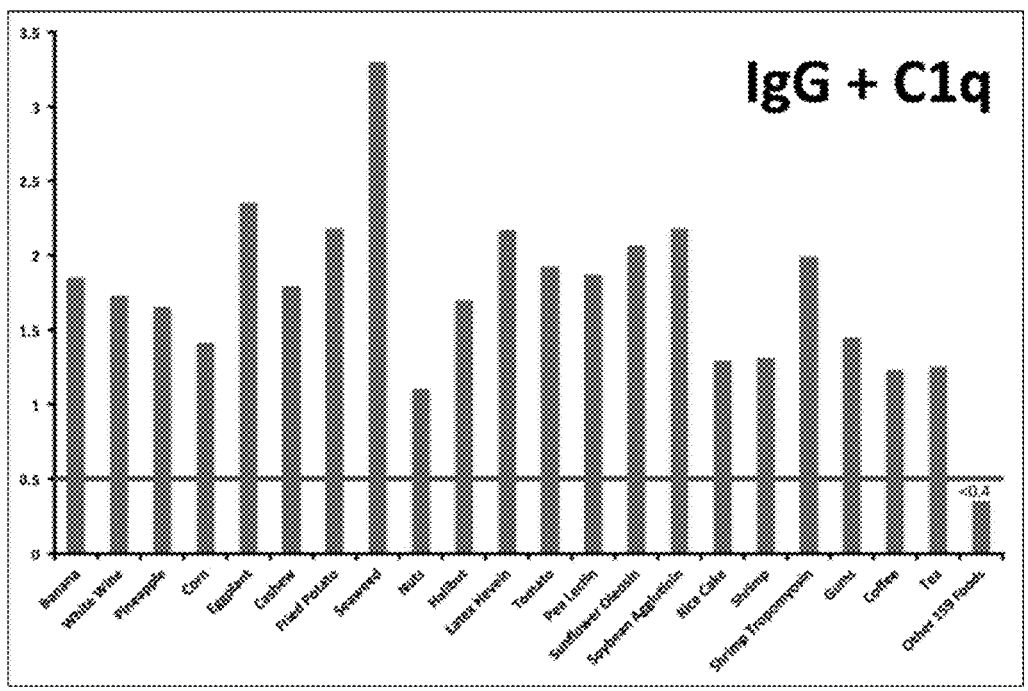
FIG. 7 shows the results of assays for both IgG and C1q binding (via native Immunoglobulin-C1q complex from a second individual to the same test surface of the inventive concept. IgG and IgC1q binding were characterized using test surfaces that included different antigen-containing extracts from 180 tested foods for the second individual. In combination, significant IgG and C1q binding was identified for 21 food antigen extracts, representing the food antigen extracts identified in individual IgG and C1q studies for this individual.

FIGS. 5, 6 and 7 show the results of similar studies with a different individual (i.e. the IgG, native Immunoglobulin-C1q complex, and IgG+native Immunoglobulin-C1q antibody profiles against 180 food extracts). Note that for IgG measurement only 10 out of 180 food extracts were reactive (FIG. 5), and when native Immunoglobulin-C1q complex was measured 14 foods were reactive (11 of which were unique to the native Immunoglobulin-C1q profile, see FIG. 6). When both IgG and native Immunoglobulin-C1q were characterized, the combined profile indicates reactivity to 21 food extracts are elevated (as shown in FIG. 7). This combined profile represents a combination of the 10 food antigens detected by IgG (shown in FIG. 5) and the additional 11 detected for native Immunoglobulin-C1q complex (shown in FIG. 6).

This demonstrates that for optimal detection of food immune reactivity, a combination of IgG plus native Immunoglobulin-C1q complex profile should be generated, utilizing test surfaces coated with a combination of different antigen populations derived from each food tested.

FIGS. 8, 9, 10, and 11 depict tabular results of studies of anti-IgG plus anti-C1q antibody binding against serum-treated test surfaces coated with antigens derived from four different sets of foods, respectively. Test surfaces were coated with different antigen preparations, including commercial food antigen preparations that contain mainly water-soluble components, non-commercial water-soluble proteins extracted as described above, non-commercial alcohol-soluble proteins extracted as described above, non-commercial alkali-soluble proteins extracted as described above, non-commercial glycolipids extracted as described above, non-commercial polysaccharides extracted as described above, and non-commercial glycoproteins extracted as described above. Results are shown for test surfaces coated with individual antigen preparations and for test surfaces coated with a combination of all six non-commercial antigen preparations. In addition, the result from surfaces treated with a combination of non-commercial antigen preparations from heat-treated/cooked foods are shown. Results showing an optical density greater than 0.5 were considered positive for this data set.

While there is good correlation between antibody detection against commercial food antigen preparations and the water-soluble food components, significant differences in immune reactivity are found when these measurements compared to those obtained with alcohol-soluble, alkali-soluble, glycolipid, polysaccharide and glycoprotein components. Similar differences are seen in comparisons with test surfaces coated sequentially with this such of food antigen preparations.

For example, when IgG and native IgG-Cq complex binding was characterized against commercial banana extract (see FIG. 8), the result is an optical density (OD) of 0.58, or vey weakly positive. Using a water-soluble extract prepared as above, the OD became 0.65, which is weakly positive (or "+"). But when characterized against banana polysaccharides, the O.D. rose to 0.98 or (++), and with the mixture of all six extracts the OD rose to 1.73 (++++). Similarly, using the heat-denatured mixture of banana antigens the resulting OD was 1.48 (+++). These findings demonstrate that strong immune reactivity against banana would have gone undetected if only commercial antigens had been used in the assay.

A similar pattern was seen with corn (see FIG. 8). When IgG plus native Immunoglobulin-C1q complex was measured the result was an O.D. of 0.48 or (±) against the commercial corn extract, 0.56 or (+) with a water-soluble extract, 1.4 or (+++) with an alcohol-soluble extract, 0.93 or (++) with an alkali-soluble extract, 0.72 or (+) with a glycolipid preparation, and 0.86 or (++) with a polysaccharide preparation. When measured against a test surface coated sequentially with these six extracts, the O.D. was 2.84 or (+++++), indicating a high degree of immune reactivity.

Mushroom (see FIG. 9) is another good example, with immune reactivity rising from an O.D. of 0.45 or (±) with the commercial extract, to 3.11 (+++++) with a water-soluble extract, even rising to 3.52 (++++++) using a test surface treated sequentially with all heat-denatured antigen preparations. Likewise, the O.D.s for pea (FIG. 9), potato (FIG. 9), rice (FIG. 10), sesame seed (FIG. 10), spinach (FIG. 10), tomato (FIG. 10), wheat (FIG. 10), and egg yolk (FIG. 10) bear examination. Against egg yolk, water-soluble extract components detected practically no IgG or native Immunoglobulin-C1q complex (−), however the O.D. went up to 0.36 with alcohol-soluble components and to 3.31 (+++++) when a test surface sequentially coated with all antigen preparation was used. With egg white (FIG. 10), which has water-soluble proteins, a similar reactivity of (++++) was observed. Similar results were also detected with shrimp (FIG. 11), almond (FIG. 11), brazil nut (FIG. 11), peanut (FIG. 11), and wheat.

It is notable that in the case of shrimp and almond the binding of IgG and native Immunoglobulin-C1q complex changed significantly when measured using test surfaces coated sequentially with all the antigen preparations. It should also be noted that while heat denaturation resulted in the reduction of O.D.s from 2.76 (+++++) to 1.2 (++) when the extract mix was used for shrimp, heat denaturation of the mixture resulted in immune reactivity being enhanced for almond from 0.5 to 1.6, and for Brazil nut from 1.36 to 2.49. As a final example, the O.D. of IgG plus native Immunoglobulin-C1q complex against peanut went up from 1.51 with commercial extract to 2.18 when test surfaces coated sequentially with all extracts were used, and rose further to 3.98 when the mix was heat-denatured.

This shows that for more accurate characterization of IgG and/or C1q containing immune complexes, test surfaces coated sequentially with extracts made from water-soluble components, alcohol-soluble components, alkali-soluble components, glycolipids, polysaccharides, glycoproteins prepared from foods in their raw form and, when applicable, in heat denatured or cooked form, should be used to produce the most complete binding profile.

It should be appreciated that, while results for IgG from samples are noted above, similarly improved results are expected from testing for IgA binding to test surfaces of the inventive concept. It should also be appreciated that characterization of IgE, IgM, and/or IgD binding to test surfaces of the inventive concept are expected to provide more complete, sensitive, and/or accurate assessments of antibody response to food antigens than those obtained from test surfaces prepared using a single antigen extraction or preparation method from each food. In some embodiments of the inventive concept, different antibody species can be tested in combination utilizing the same test surface. For example, both IgG and IgA binding to the same test surface can be determined simultaneously. Similarly, IgG, IgA, and IgE to the same test surface can be determined simultaneously. In other embodiments of the inventive concept, IgG and IgE binding to the same test surface can be determined simultaneously. In still other embodiments, IgA and IgE binding to the same test surface can be determined simultaneously.

It should also be appreciated that, although C1q was specifically cited above, similarly improved results are expected from testing for other complement species in concert with one or more of IgG, IgA, IgM, IgE, and/or IgD. Suitable complement components include participants in the classical complement pathway, including C1r and/or C1s. In some embodiments C1q, C1r, and/or C1s are characterized in concert (i.e. simultaneously) with one or more of IgG, IgA, IgE, IgM, and/or IgD using the same test surface. Similarly, one or more of C4, C2, C4a, C4b, C2a, C2b C3, C3a, and C3b can be characterized in concert with one or more of C1q, C1r, C1s, IgG, IgA, IgE, IgM, and/or IgD using the same test surface.

REFERENCES

1. Vojdani A. A potential link between environmental triggers and autoimmunity. *Autoimmune Diseases*. Volume 2014, Article ID 437231, 18 pages. http://dx.doi.org/10.115/2014/437231, 2014.
2. Vojdani A. Food immune reactivity and neuroautoimmunity. *Funct Neurol Rehabil Ergon*. 2014; 4(2-3):175-195.
3. Johnston L K, Chen K B, Bryce P J. The immunology of food allergy. *J. Immunol*. 2014; 192:2529-2534.
4. Vojdani A, Kharrazian D, Mukherjee P S. The prevalence of antibodies against wheat and milk proteins in blood donors and their contribution to neuroautoimmune reactivities. *Nutrients*. 2014; 6:15-36.
5. Ho M H, Wong W H, Chang C. Clinical spectrum of food allergies: a comprehensive review. *Clin. Rev. Allergy Immunol*. 2012; DOI:10.1007/s12016-012-8339-6.
6. Miyajima I, Dombrowicz S, Martin T R, Ravetch J V, Kinet J P, Galli S J. Systemic anaphylaxis in the mouse can be mediated largely through IgG1 and Fc gammaRIII. Assessment of the cardiopulmonary changes, mast cell degranulation, and death associated with active or IgE- or IgG1-dependent passive anaphylaxis. *J. Clin. Invest*. 1997; 99:901-914.
7. Strait R T, Morris S C, Yang M, Qu X W, Finkelman F D. Pathways of anaphylaxis in the mouse. *J. Allergy Clin. Immunol*. 2002; 109: 658-668.
8. Smit J J, Willemsen K, Hassing I, Fiechter D, Storm G, van Bloois L, Leusen J H, Pennings M, Zaiss D, Pieters R H. Contribution of classic and alternative effector pathways in peanut-induced anaphylactic responses. *PLoS ONE*. 2011; 6:e28917.
9. Mancardi D A, Albanesi M, Jonsson F, Iannascoli B, Van Rooijen N, Kang X, England P, Daëron M, Bruhns P. The high-affinity human IgG receptor FcgRI (CD64) promotes IgG-mediated inflammation, anaphylaxis, and antitumor immunotherapy. *Blood*. 2013; 121:1563-1573.
10. Lim P L, Rowley D. The effect of antibody on the intestinal absorption of macromolecules and on intestinal permeability in adult mice. *Int Arch Allergy Appl Immunol* 1982; 68.41-46.
11. Tsuji N M, Kosaka A. Oral tolerance: intestinal homeostasis and antigen-specific regulatory T cells. *Trends Immunol*. 2008; 29(11):532-540. Doi10.1016/j.it.2008.09.002.
12. Maul J, Dichmann R. Can loss of immune tolerance cause IBD? *Inflamm Bowel Dis*. 2008; 14(2):S115-S116.
13. Brandtzaeg P, Tolo K. Mucosal penetrability enhanced by serum-derived antibodies. *Nature*. 1977; 266.262-263.

14. Barnes R M R. IgG and IgA antibodies to dietary antigens in food allergy and intolerance. *Clin Exp Allergy.* 1995; 25:7-9.
15. Schrander J J, Mracelis C, de Vries M P, van Santen-Hoeufft H M. Does food intolerance play a role in juvenile chronic arthritis? *Br J Rheumatol.* 1997; 36:905.
16. Lunardi C, Bambara L M, Biasi D, Zagni P, Caramaschi P, Pacor M L. Elimination diet in the treatment of selected patients with hypersensitivity vasculitis. *Clin Exp Rheumatol.* 1992; 10:131.
17. Lunardi C, Nanni L, Tiso M, et al. glycine-rich cell wall proteins act as specific antigen targets in autoimmune and food allergic disorders. *Int Immunol.* 2000; 12:647-657.
18. Baboonian C, Halliday D, Venables P J W, Pawlowski T, Millman G, Maini R N. Antibodies in rheumatoid arthritis react specifically with the glycine alanine repeat sequence of Epstein-Bar nuclear antigen-1. *Rheumatol Int.* 1989; 9:161.
19. Baboonian C, Venavles P J W, Williams D G, Williams R O, Maini R N. Cross reaction of antibodies to glycine/alanine repeat sequence of Epstein-Barr virus nuclear antigen-1 with collagen, cytokeratin, and actin. *Ann Rheum Dis.* 1991; 50:772.
20. Ostenstad B, Dybwad A, Lea T, Forre O, Vinje O, Sioud M. Evidence for monoclonal expansion of synovial T cells bearing V alpha 2.1/V beta 5.5 gene segments and recognizing a synthetic peptide that shares homology with a number of putative autoantigens. *Immunology.* 1995; 86:168.
21. Zuidmeer L, Goldhan K, Rona R J, Gislason D, Madsen C, Summers C, Sodergreen E, Dahlstrom J, Lindner T, Sigurdardottir S T, et al. The prevalence of plant food allergies: A systemic review. *J Allergy Clin Immunol.* 2008; 121,1210-1218.
22. Lack G. Epidemiologic risks for food allergy. *J Allergy Clin Immunol.* 2008; 121:1331-1336.
23. Bousquet J, Bjorkstén B, Bruijnzeel-Koomen C A, Huggett A, Ortolani C. Warner J O, Smith M. Scientific criteria and selection of allergenic foods for product labelling. *Allergy.* 1998; 53,3-21.
24. Arentz-Hansen H, Korner R, Molberg Ø, et al. The intestinal T cell response to α-gliadin in adult celiac disease is focused on a single deamidated glutamine targeted by tissue transglutaminase. *J Exp Med.* 2000; 191(4)603-312.
25. Arentz-Hansen H, Mcadam S N, Molberg O, et al. Celiac lesion T cells recognize epitopes that cluster in regions of gliadins rich in proline residues. *Gastroenterology.* 2002; 123(3)803-809.
26. Tollefsen S, Arentz-Hansen H, Flechenstein B, et al. HLA-DQ2 and -DQ8 signatures of gluten T cell epitopes in celiac disease. *J Clin Invest.* 2006; 116(8)2226-2236.
27. Camarca A, Anderson R P, Mamone G, et al. Intestinal T cell responses to gluten peptides are largely heterogeneous: implications for a peptide-based therapy in celiac disease. *J Immunol.* 2009: 182(7)4158-4166.
28. Vojdani A. The characterization of repertoire of what antigen and peptide involved in the humoral immune response in patients with gluten sensitivity and Crohn's disease. *ISRN Allergy.* 2011; 2011,950104.
29. De Freitas I N, Sipahi A M, Damiao A O, de Brito T, Cancado E L, Leser P G, Laudanna A A. Celiac disease in Brazilian adults. *J Clin Gasroenterol.* 2002; 34:430-434.
30. Gillett P M, Gillett H R, Israel D M, Metzger D L, Stewart L, Chanoine J P, Freeman H J. High prevalence of celiac disease in patients with type I diabetes detected by antibodies to endomysium and tissue transglutaminase. *Can J Gastorenterol.* 2001; 15:297-301.
31. Counsell C E, Taha A, Ruddell W S J. Coeliac disease and autoimmune thyroid disease. *Gut.* 1994; 35:844-846.
32. Vojdani A, Tarash I. Cross-reaction between gliadin and different food and tissue antigens. *Food Nutr Sci.* 2013; 44,20-32.
33. Hadjivassiliou M, Sanders D S, Woodroofe N, Williamson C, Grunewald R A. Gluten ataxia. *Cerebellum.* 2008; 7:494-98.
34. Stamnaes J, Dorum S, Fleckenstein B, Aeschlimann D, Sollid L M. Gliadin T-cell epitope targeting by TG3 and TG6: implications for gluten ataxia and dermatitis hypertiformis. Proceedings of the 13th International Symposium on Coeliac Disease. Amsterdam. 2009; P-163:148.
35. Stagi S, Giani T, Simoni G, Falcini F. Thyroid function, autoimmune thyroiditis and coeliac disease in juvenile idiopathic arthritis. *Rheumatology.* 2005; 44:517-520.
36. Vojdani A, O'Bryan T, Green J A, McCandless J, Woeller K N, Vojdani E, Nourian A A, Cooper E L. Immune response to dietary proteins, gliadin and cerebellar peptides in children with autism. *Nutr. Neurosci.* 2004; 7,151-161.
37. Alaedini A, et al. Immune cross-reactivity in celiac disease: anti-gliadin antibodies bind to neuronal synapsin I. *J. Immunol.* 2007; 178:6590-6595.
38. Jacob S, Zarei M, Kenton A, Allroggen H. Gluten sensitivity and neuromyelitis optica: two case reports. *J Neurol Neurosurg Psychiatry.* 2005; 76:1028-1030.
39. Reinke Y, Behrendt M, Schmidt S, Zimmer K P, Naim H Y. Impairment of protein trafficking by direct interaction of gliadin peptide with actin. *Exp Cell Res.* 2011; DOI:10.1016/J.YXCT.2011.05.022.
40. Hadjivassiliou M, Sanders D S, Grünewald R A, Akil M, Gluten sensitivity masquerading as systemic lupus erythematosus. *Ann Rhem Dis.* 2004; 63:1501-1503.
41. Sugai E, Chernaysky A, Pedreira S, et al. Bone-specific antibodies in sera from patients with celiac disease: characterization and implications in osteoporosis. *J Clin Immunol.* 2002; 22:353-362.
42. Collin P, Kaukinen K, Välimäki M, Salmi J. Endocrinological disorders and celiac disease. *Endoc Rev.* 2002; 23:464-483.
43. Frustaci A, Cuoco L, Chimenti C, et al. Celiac disease associated with autoimmune myocarditis circulation. 2002; 2:2611-2618
44. Pratesi R, Gandolfi L, Friedman H, et al. Serum IgA antibodies from patients with coeliac disease react strongly with human brain blood-vessel structures. 1998; 33:817-821.
45. Natter S, Granditsch G. Reichel G L, et al. IgA cross-reactivity between a nuclear autoantigen and wheat protein suggests molecular mimicry as a possible pathomechanism in celiac disease. *Eur J Immunol.* 2001; 31:918-928.
46. Kahana E, Zilber N, Abramson J H, Biton V, Leibowitz Y, Abramsky O. Multiple sclerosis: genetic versus environmental aetiology. Epidemiology in Israel updated. *J Neurol.* 1994; 241:341-346.
47. Agranoff B W A, Goldberg D. Diet and the geographical distribution of multiple sclerosis. *Lancet* 1974; 2:1061-1066.
48. Knox E G. Foods and diseases. *Br. J. Prev. Soc. Med.* 1977; 31:71-80.
49. Butcher J. The distribution of multiple sclerosis in relation to the dairy industry and milk consumption. *N.Z. Med. J.* 1976; 83:427-430.

50. Malosse D, Perron H, Sasco A, Seigneurin J M. Correlatoin between milk and dairy product consumption and multiple sclerosis prevalence: a worldwide study. *Neuroepidemiol.* 1992; 11:304-312.
51. Henry J, Miller M M, Pontarotti P P. Structure and evolution of the extended B7 family. *Immunol. Today.* 1999; 20:285.
52. Gardinier M V, Amiguet P, Limington C, Matthieu J M. Myelin/oligodendrocyte glycoprotein is a unique member of the immunoglobulin super-family. *J. Neurosci. Res.* 1992; 33:177.
53. Jack L J, Mather I H, Cloning and analysis of cDNA encoding bovine butyrophilin, and apical glycoprotein expressed in mammary tissue and secreted in association with the milk-fat globule membrane during lactation. *J. Biol. Chem.* 1990; 265:14481.
54. Vojdani A, Campbell A, Anyanwu E, Kashanian A, Bock K, Vojdani E. Antibodies to neuron-specific antigens in children with autism: Possible cross reaction with encephalitogenic proteins from milk. *Chlamydia pneumonia* and *Streptococcus* Group A. *J. Neuroimmunol.* 2002; 129:168-177.
55. Amor S, Groome N, Linington C, Morris M M, Dornmair K, Gardinier M V, Matthieu J M, Baker D. Identification of epitopes of myelin oligodendrocyte glycoprotein for the induction of experimental allergic encephalomyelitis in SJL and Biozzi AB/H mice. *J. Immunol.* 1994; 153:4349.
56. Jarius S, et al. Mechanisms of disease: aquaporin-4 antibodies in neuromyelitis optica. *Nat. Clin. Pract. Neurol.* 2008; 4:202-214.
57. Jarius S, Wildermann B. AQP4 antibodies in neuromyelitis optica: diagnostic and pathogenetic relevance. *Nat. Rev. Neurol.* 2010; 6:383-392.
58. Kim S H, et al. Clinical spectrum of CNS aquaporin-4 autoimmunity. *Neurol.* 2012; 78:1179-1185.
59. Kinoshita M, et al. Anti-aquaporin-4 antibody induces astrocytic cytotoxicity in the absence of CNS antigen-specific T cells. *Biochem. Biophys. Re.s Commun.* 2010; 394:205-210.
60. Bradl M, Lassmann D H. Anti-aquaporin-4 antibodies in neuromyelitis optica: how to prove their pathogenetic relevance? *Int. MS J.* 2008; 15:75-78.
61. Vaishnav R, et al. Aquaporin-4 molecular mimicry and implication for neuromyelitis optics. *J. Neuroimmunol.* 2013; 26:92-98.
62. Plasencia I, et al. Structure and stability of the spinach aquaporin SoPIP2:1 in detergent micelles and lipid membranes. *PLoS One.* 2011; 6:e14674.
63. Fleurat-Lassard P, et al. The distribution of aquaporin subtypes (PIP1, PIP2 and gamma-TIP) is tissue dependent in soybean (Glycine Max) root nodules. *Ann. Bot.* 2005; 96:457-460.
64. Fabian C, Ju Y-H; A review on rice bran protein: its properties and extraction methods. Crit Rev Food Sci Nutr. 2011; 51:816-827.
65. Hamada J S. Characterization of protein fractions of rice bran to devise effective methods of protein solubilization. Cereal Chem. 1997; 74:662-668.
66. Singh N K, Donovan G R, Batey I L, et al. Use of sonication and size-exclusion HPLC in the study of wheat flour protein. I. Dissolution of total protein in unreduced form. Cereal Chem. 1990; 67:150-161.
67. Tang S, Hettiararchy N S, Shellhammer T H. Protein extraction from heat-stabilized defatted rice bran. I. Physical processing and enzyme treatments. J Agric Food Chem. 2002; 50:7444-7448.
68. Novik G I, Astapovich N I, Grzegorzewicz A, et al. Isolation and comparative analysis of glycolipids from bifidobacteria. Mikrobiology. 2005; 74(5):1-8.
69. Novik G I, Gamian A, Francisco Jda C, Dey E S. A novel procedure for the isolation of glycolipids from *Bifidobacterium adolescentis* 94 BIM using supercritical carbon dioxide. J Biotechnol. 2006; 121(4):555-62.
70. Ishikawa T, et al. Method of separating glycolipids. Pub. No: US2005/0119475 A1, Jun. 2, 2005.
71. Chaiklahan R, et al. Polysaccharide extraction from *Spirulina* sp. and its antioxidant capacity. Int J Biol Macromol. 58: 73-78, 2013.
72. Dubois M, et al. Colorimetric method for determination of sugar and related substances. Anal Chem. 28(3): 350-356, 1956.
73. Sheng J, et al. Preparation, identification and their antitumor activities in vitro of polysaccharides from *Chlorella pyrenoidosa*. Food Chem. 105(2): 533-539, 2007.
74. Vojdani A. Lectins, agglutinins, and their role in auto-immune reactivities. *Alternative Therapies in Health and Medicine*, (In Press), 2015.
75. Lamport D T. Preparation of arabinogalactan glycoproteins from plant tissues. Bio-Protocol. 3(19):10/5/2013, e918.
76. Muthukumar M, et al. Isolation, purification and biochemical characterization of lectin from oyster mushroom, *Pleurotus sajor-caju*. Plant Archives 2009; 9:41-46.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method for characterizing an antibody and complement profile for food immune reactivity in a subject, comprising:

obtaining a sample comprising one or more immunoglobulins and native Immunoglobulin-C1q complex from said subject;

providing a test surface comprising a food antigen coating, wherein the food antigen coating comprises a first food antigen, a second food antigen, and a third food antigen that have been applied to the test surface in a sequential manner;

contacting the test surface with at least a portion of the sample;

contacting the test surface with an antibody mixture, wherein the antibody mixture comprises a first antibody directed to C1q and a second antibody directed to at least one of the one or more immunoglobulins of the sample species; and obtaining a signal characteristic of binding of both at least one of the immunoglobulins and native Immunoglobulin-C1q complex from the sample to the test surface, wherein a signal intensity that exceeds a background cutoff is characterized as a positive result.

2. The method of claim 1, wherein at least one of the immunoglobulins is an IgG.

3. The method of claim 1, wherein at least one of the immunoglobulins is an IgA.

4. The method of claim 1, wherein the first food antigen, the second food antigen, and the third food antigen are obtained from the same food by different extraction methods.

5. The method of claim 1, further comprising contacting the test surface with a third antibody comprising an antibody directed to the first antibody, wherein the third antibody comprises a detectable tag.

6. The method of claim 5, further comprising contacting the test surface with a fourth antibody comprising an antibody directed to the second antibody, wherein the fourth antibody comprises a detectable tag.

7. The method of claim 1, further comprising contacting the test surface with a fifth antibody comprising an antibody directed to both the first and second antibodies, wherein the fifth antibody comprises a detectable tag.

8. The method of claim 1, wherein the first antibody further comprises a first detectable tag and the second antibody further comprises a second detectable tag.

9. The method of claim 8, wherein the first detectable tag and the second detectable tag are distinguishable.

10. A method for characterizing an antibody and complement profile for food immune reactivity in a subject, comprising:
   obtaining a sample comprising one or more immunoglobulins and one or more native Immunoglobulin-C1q complexes from said subject;
      providing a first test surface comprising a first food antigen coating, wherein the first food antigen coating comprises a first food antigen, a second food antigen, and a third food antigen that have been applied to the test surface in a sequential manner;
      providing a second test surface comprising a second food antigen coating, wherein the second food antigen coating comprises a fourth food antigen, a fifth food antigen, and a sixth food antigen that have been applied to the second test surface in a sequential manner;
   contacting the first and second test surfaces with first and second portions of the sample, respectively;
   contacting the first and second test surfaces with an antibody mixture, wherein the antibody mixture comprises a first antibody directed to C1q and second antibody directed to at least one of the immunoglobulins of the sample species;
   obtaining, from the first test surface, a first signal characteristic of binding of both at least one of the immunoglobulins and at least one of the native Immunoglobulin-C1q complexes from the sample to the first test surface, wherein a first signal intensity that exceeds a background cutoff is characterized as a positive result for the first test surface; and
   obtaining, from the second test surface, a second signal characteristic of binding of both at least one of the immunoglobulins and at least one of the native Immunoglobulin-C1q complexes from the sample to the second test surface, wherein a second signal intensity that exceeds a background cutoff is characterized as a positive result for the second test surface.

11. A test kit for characterizing antibody and C1q binding profiles for food immune reactivity to a food sample comprising (1) a test plate, wherein the test plate comprises a plurality of test surfaces, and wherein at least one of the plurality of test surfaces comprises a food antigen coating, wherein the food antigen coating comprises a first food antigen, a second food antigen, and a third food antigen that have been applied to the test surface in a sequential manner, and (2) a plurality of antibodies, wherein a first antibody directed to C1q and a second antibody directed to at least one of the one or more immunoglobulins of the sample species.

12. The test kit of claim 11, wherein the plurality of test surfaces includes a first test surface comprising antigens from a first food and a second test surface comprising antigens from a second food.

* * * * *